(12) United States Patent
Claremon et al.

(10) Patent No.: US 8,440,658 B2
(45) Date of Patent: May 14, 2013

(54) CYCLIC UREA INHIBITORS OF 11β-HYDROXYSTEROID DEHYDROGENASE 1

(75) Inventors: David A. Claremon, Maple Glen, PA (US); Linghang Zhuang, Chalfont, PA (US); Colin M. Tice, Ambler, PA (US); Yuanjie Ye, Ambler, PA (US); Wei He, Audubon, PA (US); Suresh B. Singh, Kendall Park, NJ (US); Zhenrong Xu, Chalfont, PA (US); Salvacion Cacatian, Conshohocken, PA (US); Wei Zhao, Eagleville, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 205 days.

(21) Appl. No.: 12/747,391

(22) PCT Filed: Dec. 10, 2008

(86) PCT No.: PCT/US2008/013539
§ 371 (c)(1),
(2), (4) Date: Nov. 11, 2010

(87) PCT Pub. No.: WO2009/075835
PCT Pub. Date: Jun. 18, 2009

(65) Prior Publication Data
US 2011/0263582 A1 Oct. 27, 2011

Related U.S. Application Data

(60) Provisional application No. 61/007,060, filed on Dec. 11, 2007.

(51) Int. Cl.
C07D 413/10 (2006.01)
C07D 413/14 (2006.01)
A61K 31/5355 (2006.01)

(52) U.S. Cl.
USPC .................................. 514/228.8; 544/97

(58) Field of Classification Search .................. 544/97; 514/228.8
See application file for complete search history.

(56) References Cited

U.S. PATENT DOCUMENTS

| | | |
|---|---|---|
| 3,341,538 A | 9/1967 | Block et al. |
| 3,681,349 A | 8/1972 | Schwan et al. |
| 4,136,145 A | 1/1979 | Fuchs et al. |
| 4,136,162 A | 1/1979 | Fuchs et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 7,026,310 B2 | 4/2006 | Emig et al. |
| 7,056,912 B2 | 6/2006 | Emig et al. |

(Continued)

FOREIGN PATENT DOCUMENTS

| | | |
|---|---|---|
| DE | 1801556 A1 | 5/1970 |
| DE | 19918725 A1 | 10/2000 |

(Continued)

OTHER PUBLICATIONS

Millard et al. Chimica Therapeutica (1968), 3(5), 321-4.*

(Continued)

*Primary Examiner* — Kahsay T Habte
(74) *Attorney, Agent, or Firm* — McCarter & English, LLP; Steven G. Davis; Michael J. DeGrazia

(57) ABSTRACT

Disclosed is a compound represented by Formula (I):

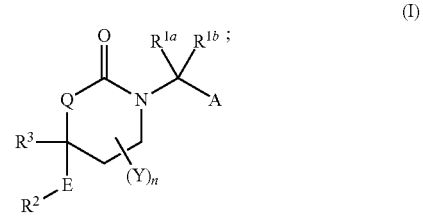

or a pharmaceutically acceptable salt, monohydrate, enantiomer or diastereomer thereof. Also disclosed are pharmaceutical compositions comprising the compound of Formula (I) or a pharmaceutically acceptable salt, monohydrate, enantiomer or diastereomer thereof and methods of inhibiting 11β-HSD1 activity comprising the step of administering to a mammal in need of such treatment an effective amount of a compound of Formula (I), or a pharmaceutically acceptable salt, monohydrate, enantiomer or diastereomer thereof. Values for the variables in Formula (I) are defined herein.

19 Claims, No Drawings

U.S. PATENT DOCUMENTS

| | | |
|---|---|---|
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0124384 A1 | 5/2008 | Blum |
| 2008/0188482 A1 | 8/2008 | Rice et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0264650 A1 | 10/2009 | Cho et al. |
| 2010/0041637 A1 | 2/2010 | Claremon et al. |
| 2010/0197675 A1 | 8/2010 | Claremon et al. |

FOREIGN PATENT DOCUMENTS

| | | |
|---|---|---|
| DE | 19929348 A1 | 12/2000 |
| DE | 100 34 623 | 1/2002 |
| DE | 10034623 | 1/2002 |
| EP | 0415642 A1 | 3/1991 |
| EP | 0454444 A1 | 10/1991 |
| EP | 0640594 A1 | 3/1995 |
| EP | 0645387 A | 3/1995 |
| EP | 0471591 | 5/1995 |
| EP | 0928789 A1 | 7/1999 |
| EP | 1156049 A | 11/2001 |
| EP | 1270724 A2 | 1/2003 |
| EP | 1852425 A | 11/2007 |
| EP | 1864971 A | 12/2007 |
| EP | 1935420 | 6/2008 |
| GB | 1077711 | 8/1967 |
| JP | 6092945 A | 4/1994 |
| JP | 7157681 | 6/1995 |
| JP | 2009110842 A2 | 4/1997 |
| JP | 09151179 | 6/1997 |
| JP | 2002179572 A2 | 6/2002 |
| JP | 2003096058 | 4/2003 |
| JP | 2003300884 A2 | 10/2003 |
| JP | 2005-206503 A | 8/2005 |
| JP | 2005239670 | 9/2005 |
| JP | 2005272321 A | 10/2005 |
| JP | 2007 140188 | 6/2007 |
| JP | 2007 254409 | 10/2007 |
| WO | WO 92/07838 | 5/1992 |
| WO | WO 93/07128 | 4/1993 |
| WO | WO 93/13103 | 7/1993 |
| WO | WO 95/31440 | 11/1995 |
| WO | WO 96/14297 A | 5/1996 |
| WO | WO 96/23787 | 8/1996 |
| WO | WO 97/36605 | 10/1997 |
| WO | WO 98/57940 | 12/1998 |
| WO | WO 99/05125 | 2/1999 |
| WO | WO 99/06395 | 2/1999 |
| WO | WO 01/00595 A1 | 1/2001 |
| WO | WO 01/44200 A2 | 6/2001 |
| WO | WO 01/55063 | 8/2001 |
| WO | WO 02/06244 A1 | 1/2002 |
| WO | WO 02/06277 A1 | 1/2002 |
| WO | WO 02/22572 A2 | 3/2002 |
| WO | WO 03/043988 A1 | 5/2003 |
| WO | WO 03/057673 A | 7/2003 |
| WO | WO 03/093261 A1 | 11/2003 |
| WO | WO 2004/004722 A1 | 1/2004 |
| WO | WO 2004/009559 A2 | 1/2004 |
| WO | WO 2004/014859 A2 | 2/2004 |
| WO | WO 2004/094375 A | 11/2004 |
| WO | WO 2005/000845 | 1/2005 |
| WO | WO 2005/086700 A2 | 9/2005 |
| WO | WO 2005/108361 | 11/2005 |
| WO | WO 2005/108361 A | 11/2005 |
| WO | WO 2005/113525 A1 | 12/2005 |
| WO | WO 2006/003494 A2 | 1/2006 |
| WO | WO 2006/014357 A | 2/2006 |
| WO | WO 2006/024627 A2 | 3/2006 |
| WO | WO 2006/024628 A | 3/2006 |
| WO | WO 2006/031715 A | 3/2006 |
| WO | WO 2006/040329 | 4/2006 |
| WO | WO 2006/044174 | 4/2006 |
| WO | WO 2006/049952 A | 5/2006 |
| WO | WO 2006/066924 A2 | 6/2006 |
| WO | WO 2006/066948 A1 | 6/2006 |
| WO | WO 2006/090792 A1 | 8/2006 |
| WO | WO 2006/104280 A | 10/2006 |
| WO | WO 2007/008529 A2 | 1/2007 |
| WO | WO 2007/051810 | 5/2007 |
| WO | WO 2007/061661 A2 | 5/2007 |
| WO | WO 2007/068330 A1 | 6/2007 |
| WO | WO 2007/079186 A2 | 7/2007 |
| WO | WO 2007/081569 A2 | 7/2007 |
| WO | WO 2007/081570 A | 7/2007 |
| WO | WO 2007/081571 A2 | 7/2007 |
| WO | WO 2007/084314 A2 | 7/2007 |
| WO | WO 2007/109456 A2 | 9/2007 |
| WO | WO 2007/118185 A2 | 10/2007 |
| WO | WO 2007/124254 | 11/2007 |
| WO | WO 2007/124329 A | 11/2007 |
| WO | WO 2007/124337 | 11/2007 |
| WO | WO 2007/127693 A | 11/2007 |
| WO | WO 2008/000951 | 1/2008 |
| WO | WO 2008/031227 A1 | 3/2008 |
| WO | WO 2008/036715 A1 | 3/2008 |
| WO | WO 2008/046758 A | 4/2008 |
| WO | WO 2008/059948 A | 5/2008 |
| WO | WO 2008/106128 | 9/2008 |
| WO | WO 2008/106128 A | 9/2008 |
| WO | WO 2008/118332 A2 | 10/2008 |
| WO | WO 2009/017664 | 2/2009 |
| WO | WO 2009/017664 A1 | 2/2009 |
| WO | WO 2009/017671 | 2/2009 |
| WO | WO 2009/061498 | 5/2009 |
| WO | WO 2009/063061 | 5/2009 |
| WO | WO 2009/075835 | 6/2009 |
| WO | WO 2009/088997 | 7/2009 |
| WO | WO 2009/094169 A | 7/2009 |
| WO | WO 2009/100872 | 8/2009 |
| WO | WO 2009/102428 | 8/2009 |
| WO | WO 2009/102460 | 8/2009 |
| WO | WO 2009/117109 | 9/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | WO 2010/010149 | 1/2010 |
| WO | WO 2010/010157 | 1/2010 |
| WO | WO 2010/010174 | 1/2010 |
| WO | WO 2010/011314 | 1/2010 |
| WO | WO 2010/023161 | 3/2010 |
| WO | WO 2010/046445 | 4/2010 |
| WO | WO 2010/091067 | 8/2010 |
| WO | WO 2010/127237 | 11/2010 |

OTHER PUBLICATIONS

International Search Report—(PCT/US2010/023021) Date of Mailing Aug. 5, 2010.
U.S. Appl. No. 12/670,205, filed Jul. 25, 2008, Vitae Pharmaceuticals, Inc.
U.S. Appl. No. 12/670,209, filed Jul. 25, 2008, Vitae Pharmaceuticals, Inc.
U.S. Appl. No. 12/741,522, filed Apr. 30, 2009, Vitae Pharmaceuticals, Inc.
U.S. Appl. No. 12/990,309, filed Apr. 30, 2009, Vitae Pharmaceuticals, Inc.
U.S. Appl. No. 12/990,296, filed Apr. 30, 2009, Vitae Pharmaceuticals, Inc.
U.S. Appl. No. 12/745,663, filed Nov. 7, 2008, Vitae Pharmaceuticals, Inc.
U.S. Appl. No. 12/811,577, filed Jan. 7, 2009, Vitae Pharmaceuticals, Inc.
U.S. Appl. No. 12/863,634, filed Jan. 21, 2009, Vitae Pharmaceuticals, Inc.
U.S. Appl. No. 12/867,374, filed Feb. 13, 2009, Vitae Pharmaceuticals, Inc.
U.S. Appl. No. 12/933,027, filed Mar. 18, 2009, Vitae Pharmaceuticals, Inc.
U.S. Appl. No. 12/741,532, filed Sep. 27, 2010, Vitae Pharmaceuticals, Inc.
U.S. Appl. No. 12/771,499, filed Apr. 30, 2010, Vitae Pharmaceuticals, Inc.
MS Bitar, "Glucocorticoid Dynamics and Impaired Wound Healing in Diabetes Mellitus", Am J Pathol., 1998, vol. 152, pp. 547-554.
MS Bitar, et al., "Heat-Shock Protein 72/73 and Impaired Wound Healing in Diabetic and Hypercortisolemic States", Sugery, 1999, vol. 125, pp. 594-601.
MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.
MS Bitar, "Insulin and Glucocorticoid-Dependent Suppression of the IGF-I System in Diabetic Wounds", Sugery, 2000, vol. 127, pp. 687-695.
Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CAS RN: 20057-45-8.
Chimica Therapeutica, 1968, vol. 3(5), pp. 321-324, 1968.
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2.
Zhurnal Organicheskoi Khimii, 1978, vol. 14(5), pp. 1092-1094.
Database CA [Online], Chemical Abstracts Service, Fukushima et al., "Preparation of Imidazolidinone Derivatives as 11.beta.—HSD1 Inhibitors", XP 002531878.
"Khimiia Elementoorganicheskikh Soedineni", 1982, vol. 1982 pp. 22-26.
"Zhurnal Organicheskoi Khimii", 1982, vol. 18, PT 11, p. 2468.
Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063.
Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064.
Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.
Ho-Jane Shue et al., "Cyclic Urea Derivatives as Potent NK1 Selective Antagonists", Bioorganic & Medicinal Chemistry Letters, 2005, vol. 15, pp. 3896-3899.
Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.
Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Malgorzata Wamil and Jonathan R. Seckl, "Inhibition of 11β-hydroxysteroid Dehydrogenase Type 1 as a Promising Therapeutic Target", Drug Discovery Today, 2007, vol. 12, pp. 504-520.
Muehlstadt, et al., "Cyclization reactions of beta, gamma-unsaturated derivatives of carbonic acid. IX.", Journal Fuer Praktische Chemie, vol. 328, 1986, pp. 163-172, XP002504062 p. 164, compound 4j.
Schoellkopf, et al., "Umsetzungen Alphametallierter Isocyanide Mit Einigen 1,3-Dipolen//Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.
Suga, Seiji et al., "N-Acyliminium Ion Pool as a Heterodiene in [4+2] Cycloaddition Reaction", Organic Letters, 2003, vol. 5, pp. 945-947.
Suga, Seiji et al., "Cycloaddition of N-Acyliminium Ion Pools with Carbon-Carbon Multiple Bonds", Bulletin of the Chemical Society of Japan, Chemical Society of Japan, 2005, vol. 78, pp. 1206-1217.
Tamaru et al., "Urea as the Most Reactive and Versatile Nitrogen Nucleophile for the Palladium(2+)-Catalyzed Cyclization of Unsaturated Amines", Journal of the American Chemical Society, 1988, vol. 110, pp. 3994-4002.
Yoshida, Masaaki et al., "Selective synthesis of five-and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.
Yoshinao Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.
International Search Report & Written Opinion—(PCT/US2008/009017) Date of Mailing Apr. 12, 2008.
International Search Report & Written Opinion—(PCT/US2008/002517) Date of Mailing Dec. 29, 2008.
International Search Report—(PCT/US2009/002653) Date of Mailing Jul. 3, 2009.
International Search Report—(PCT/US2009/002641) Date of Mailing Jul. 3, 2009.
International Search Report—(PCT/US2009/002629) Date of Mailing Jul. 3, 2009.
International Search Report—(PCT/US2009/002633) Date of Mailing Jul. 3, 2009.
International Search Report—(PCT/US2008/012618) Date of Mailing Dec. 3, 2009.
International Search Report—(PCT/US2009/000057) Date of Mailing Mar. 25, 2009.
International Search Report—(PCT/US2008/013539) Date of Mailing Mar. 19, 2009.
International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Columbus, Ohio, US, 2007, Database accession No. 958700-63-5, Abstract, XP002556893.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958629-39-5, Abstract, XP002556896.

Database File Registry [Online], Chemical Abstracts Service, Columbus, Ohio, US, 2007, Database accession No. 958629-22-6, Abstract, XP002556897.

Database File Registry [Online], Chemical Abstracts Service, Columbus, Ohio, US, 2007, Database accession No. 958629-14-6, Abstract, XP002556898.

Database File Registry [Online], Chemical Abstracts Service, Columbus, Ohio, US, 2007, Database accession No. 958625-83-7, Abstract, XP002556899.

Database File Registry [Online], Chemical Abstracts Service, Columbus, Ohio, US, 2007, Database accession No. 958599-31-0, Abstract, XP002556900.

Database CA [Online], Chemical Abstracts Service, Fukushima et al., "Preparation of Imidazolidinone Derivatives as 11.beta.-HSD1 Inhibitors", 2007, XP 002531878.

Gavezzotti, "Are Crystal Structures Predictable?", Accounts of Chemical Research, 1994, vol. 27, pp. 309-314.

Vippagunta, et al., "Crystalline Solids", Advanced Drug Deliver Reviews, 2001, vol. 48, pp. 3-26.

International Search Report and Written Opinion—(PCT/US2009/004261) Date of mailing Dec. 4, 2008.

International Search Report—(PCT/US2009/004261) Date of Mailing Oct. 21, 2009.

Shibata, et al., "Cycloaddition of Oxetanes with Heterocumulenes Catalysed by Organotin Iodine-Lewis Base Complex", Journal of Heterocyclic Chemistry, vol. 24, 1987, pp. 361-363.

* cited by examiner

CYCLIC UREA INHIBITORS OF 11β-HYDROXYSTEROID DEHYDROGENASE 1

RELATED APPLICATION

This application claims the benefit of U.S. Provisional Application No. 61/007,060, filed Dec. 11, 2007. The entire teachings of the above application is incorporated herein by reference.

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9).

Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-

HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states; such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043,951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula I or pharmaceutically acceptable salts thereof are effective inhibitors of 11β-HSD1. Formula I and its constituent members are defined herein as follows:

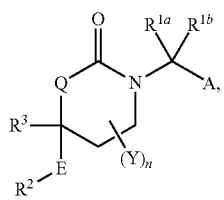

I wherein

R$^{1a}$ and R$^{1b}$ are each independently selected from (a) hydrogen or (b) (C$_1$-C$_6$)alkyl, (C$_2$-C$_6$)alkenyl, (C$_2$-C$_6$)alkynyl or (C$_1$-C$_3$)alkoxy(C$_1$-C$_3$)alkyl which are optionally substituted with up to three groups independently selected from fluorine, hydroxy, (C$_1$-C$_3$)alkoxy and H$_2$NC(=O);

A is straight or branched (C$_1$-C$_8$)alkyl, (C$_2$-C$_8$)alkenyl or (C$_2$-C$_8$)alkynyl, optionally substituted with up to 4 groups independently selected from fluorine, cyano, oxo, R$^4$, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN)NR$^4$—, (R$^4$O)$_2$P(=O)O, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, heterocyclylamino (wherein the heterocyclyl portion is optionally substituted by alkyl, haloalkyl or oxo); heteroarylamino (wherein the heteroaryl portion is optionally substituted by alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo); arylamino (wherein the aryl portion is optionally substituted by alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo); and cycloalkylamino (wherein the cycloalkyl portion is optionally substituted by alkyl, haloalkyl or oxo);

Y is (C$_1$-C$_6$)alkyl or halo(C$_1$-C$_6$)alkyl;

n is 0, 1 or 2;

E is (a) a bond or (b) (C$_1$-C$_3$)alkylene or (C$_1$-C$_2$)alkylenyloxy, wherein the O is attached to R$^2$, each of which is optionally substituted with 1 to 4 groups independently selected from methyl, ethyl, trifluoromethyl or oxo;

R$^2$ is (C$_1$-C$_6$)alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy (C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkylhio, (C$_4$-C$_7$)cycloalkylalkylthio, halo(C$_1$-C$_6$)alkylthio, halo(C$_3$-C$_6$)cycloalkylhio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkanesulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cyclo-alkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclosulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkylamino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxy, (C$_1$-C$_6$)alkylcarbonyl, (C$_3$-C$_6$)cycloalkylcarbonyl, (C$_3$-C$_6$)cycloalkylaminocarbonyl, {(C$_3$-C$_6$)cycloalkyl}{(C$_1$-C$_6$)alkyl}aminocarbonyl, di(C$_3$-C$_6$)cycloalkylaminocarbonyl, (C$_3$-C$_6$)cycloalkylaminosulfonyl, {(C$_3$-C$_6$)cycloalkyl}{(C$_1$-C$_6$)alkyl}aminosulfonyl, di(C$_3$-C$_6$)cycloalkylaminosulfonyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$)alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl(C$_1$-C$_6$)alkyl and di(C$_3$-C$_6$)cycloalkylaminocarbonyl(C$_1$-C$_6$)alkyl;

R$^3$ is selected from (C$_1$-C$_6$)alkyl, (C$_2$-C$_6$)alkenyl, (C$_2$-C$_6$)alkynyl, (C$_3$-C$_5$)cycloalkyl(C$_1$-C$_4$)alkyl, (C$_1$-C$_3$)alkoxy(C$_1$-C$_3$)alkoxy, or (C$_1$-C$_3$)alkoxy(C$_1$-C$_3$)alkyl and is optionally substituted with up to four groups independently selected from fluorine, cyano, oxo, R$^4$, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN)NR$^4$—, (R$^4$O)$_2$P(=O)O—, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, CO$_2$H, CONH$_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

Q is O or $NR^5$;

$R^5$ is H, $(C_1-C_6)$alkyl, halo$(C_1-C_6)$alkyl, or hydroxy$(C_1-C_6)$alkyl;

provided that if (a) Q is O, (b) A is optionally substituted $C_1-C_3$ alkyl; (c) $R^3$ is an optionally substituted $C_1-C_6$ alkyl; (d) then $E-R^2$ is not phenyl substituted with two groups; the two groups being at the meta and para position of the phenyl relative to the point of attachment to the oxazinone ring, wherein the two groups are independently selected from $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl$(C_1-C_6)$alkoxy, hydroxy$(C_1-C_6)$alkoxy, amino$(C_2-C_6)$alkoxy, $(C_1-C_6)$alkylamino$(C_2-C_6)$alkoxy, and di$(C_1-C_6)$alkylamino$(C_2-C_6)$alkoxy; and provided that if (a) Q is $NR^5$; (b)A is $C_1-C_5$ alkyl (c) $R^3$ is methyl or vinyl (d) then $E-R^2$ is not methyl or phenyl;

or a pharmaceutically acceptable salt, enantiomer or diastereomer thereof.

A second embodiment of the invention is a compound of Formula I wherein the values are:

$R^{1a}$ and $R^{1b}$ are each independently selected from (a) hydrogen or (b) $(C_1-C_6)$alkyl, $(C_2-C_6)$alkenyl, $(C_2-C_6)$alkynyl or $(C_1-C_3)$alkoxy$(C_1-C_3)$alkyl which are optionally substituted with up to three groups independently selected from fluorine, hydroxy, $(C_1-C_3)$alkoxy and $H_2NC(=O)$;

A is straight or branched $(C_1-C_8)$alkyl, $(C_2-C_8)$alkenyl or $(C_2-C_8)$alkynyl, optionally substituted with up to 4 groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, heterocyclylamino (wherein the heterocyclyl portion is optionally substituted by alkyl, haloalkyl or oxo); heteroarylamino (wherein the heteroaryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); arylamino (wherein the aryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and cycloalkylamino (wherein the cycloalkyl portion is optionally substituted by alkyl, haloalkyl or oxo);

Y is $(C_1-C_6)$alkyl or halo$(C_1-C_6)$alkyl;

n is 0, 1 or 2;

E is (a) a bond or (b) $(C_1-C_3)$alkyl or $(C_1-C_2)$alkoxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

$R^3$ is selected from $(C_1-C_6)$alkyl, $(C_2-C_6)$alkenyl, $(C_2-C_6)$alkynyl and $(C_1-C_3)$alkoxy$(C_1-C_3)$alkyl and is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

Q is O or $NR^5$;

$R^5$ is H, $(C_1-C_6)$alkyl, halo$(C_1-C_6)$alkyl, or hydroxy$(C_1-C_6)$alkyl;

or a pharmaceutically acceptable salt, enantiomer or diastereomer thereof.

Another embodiment is a pharmaceutical composition comprising: i) the compound of Formula I or a pharmaceutically acceptable salt, enantiomer or diastereomer thereof; and ii) a pharmaceutically acceptable carrier or diluent.

Another embodiment is a method of treating a subject with a disease associated with the activity or expression of 11β-HSD1, comprising the step of administering to the subject an effective amount of a compound of Formulas I, Ia, or Ib, or a pharmaceutically acceptable salt, enantiomer or diastereomer thereof.

Another embodiment of the invention is a compound of Formulas I, Ia, or Ib, or a pharmaceutically acceptable salt, enantiomer or diastereomer thereof for use in for treating a subject with a disease associated with the activity or expression of 11β-HSD1.

Another embodiment of the invention is the use of a compound of Formulas I, Ia, or Ib, or a pharmaceutically acceptable salt, enantiomer or diastereomer thereof for the manufacture of a medicament for treating a subject with a disease associated with the activity or expression of 11β-HSD1.

Another embodiment of the invention is a method of inhibiting 11β-HSD1 activity comprising the step of administering to a mammal in need of such treatment an effective amount of a compound of Formulas I, Ia, or Ib, or a pharmaceutically acceptable salt, enantiomer or diastereomer thereof.

Another embodiment of the invention is the use of a compound of Formulas I, Ia, or Ib, or a pharmaceutically acceptable salt, enantiomer or diastereomer thereof for the manufacture of a medicament for inhibiting 11β-HSD1 activity in a mammal in need of such treatment.

Another embodiment of the invention is a compound of Formulas I, Ia, or Ib or a pharmaceutically acceptable salt, enantiomer or diastereomer thereof for use in inhibiting 11β-HSD1 activity in a mammal in need of such treatment.

Another embodiment is a compound of Formulas I, Ia, or Ib, or a pharmaceutically acceptable salt, enantiomer or diastereomer thereof, wherein any one of the following provisos apply or any combination thereof:

Proviso 1:
If Q is $NR^5$; and if $R^3$ is methoxymethyl substituted with heteroaryl and optionally substituted with one or more additional groups, then E-$R^2$ cannot be optionally substituted heteroaryl or phenyl.

Proviso 2:
If (a) Q is O, (b) A is optionally substituted $C_1-C_5$ alkyl; (c) $R^3$ is an optionally substituted $C_1-C_6$ alkyl; (d) then E-$R^2$ is not phenyl substituted with two groups; the two groups being at the meta and para position of the phenyl relative to the point of attachment to the oxazinone ring, wherein the two groups are independently selected from $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl$(C_1-C_6)$alkoxy, hydroxy$(C_1-C_6)$alkoxy, amino$(C_2-C_6)$alkoxy, $(C_1-C_6)$alkylamino$(C_2-C_6)$alkoxy, and di$(C_1-C_6)$alkylamino$(C_2-C_6)$alkoxy.

Proviso 3:
If (a) Q is O; (b) A is alkyl, alkenyl, alkynyl optionally substituted with alkyl, alkoxy, oxo, carboxy, alkoxycarbonyl, hydroxy, mercapto, fluorine, sulfonyl, and amino; (c) $R^3$ is an alkyl, alkenyl, alkynyl optionally substituted with alkyl, alkoxy, oxo, carboxy, alkoxycarbonyl, hydroxy, mercapto, fluorine, sulfonyl, and amino; (d) then E-$R^2$ is not alkyl, aryl, cycloalkyl each optionally substituted with alkyl, alkenyl, alkynyl, aryl, alkoxy, oxo, carboxy, alkoxycarbonyl, hydroxy, mercapto, halogen, sulfonyl, or amino.

Proviso 4:
$R^3$ is other than methyl substituted with i) oxo and ii) —$OR^4$, wherein $R^4$ is hydrogen, alkyl, haloalkyl, aminoalkyl; hydroxyalkyl; and alkoxyalkyl; and $R^3$ is other than $C_1-C_4$ alkyl optionally substituted with fluorine or $C_1-C_2$ alkoxy; and E-$R^2$ is other than methyl substituted with i) oxo and ii) hydroxy; haloalkoxy, alkoxy, alkoxycarbonylalkoxy, alkoxyalkyl; and E-$R^2$ is other than $C_1-C_4$ alkyl or phenylmethyl each optionally substituted with halogen or $C_1-C_2$ alkoxy.

Proviso 5:
E-$R^2$ or $R^3$ are not both a $C_1-C_6$ alkyl, optionally substituted with an amino, thio, or alkoxy group.

Proviso 6:
If (a) A is alkyl optionally substituted with hydroxy or alkoxy; and (b) $R^3$ is alkyl optionally substituted with hydroxy or alkoxy; or alkoxyalkyl substituted with oxo; (c) then (i) E-$R^2$ is not alkyl optionally substituted with hydroxy or alkoxy; and (ii) E-$R^2$ is not unsubstituted cycloalkyl or unsubstituted aryl and (iii) E is not alkoxy and $R^2$ is not alkyl substituted with oxo and (iv) E-$R^2$ is not phenyl or phenylmethyl each optionally substituted with $C_1-C_4$ alkoxy or halogen.

Proviso 7:
If (a) Q is $NR^5$; (b) A is not methyl substituted with i) oxo and ii) alkylamino, heterocyclylamino, heteroarylamino, arylamino and cycloalkylamino.

Proviso 8:
If A is alkyl optionally substituted with oxo, carboxy, hydroxy, hydroxyalkyl, alkoxycarbonyl, sulfoxide; or alkenyl substituted with alkyl, hydroxyalkyl, or oxo; then $R^3$ and E-$R^2$ can not both be selected from the following: alkyl optionally substituted with oxo, carboxy, alkoxycarbonyl, sulfoxide, hydroxy, hydroxyalkyl; or alkenyl substituted with alkyl, hydroxyalkyl, or oxo.

Proviso 9:
If (a) Q is $NR^5$; (b) A is $C_1-C_5$ alkyl (c) $R^3$ is methyl or vinyl (d) then E-$R^2$ is not methyl or phenyl.

Another embodiment of the present invention is a compound of Formulas I, Ia, or Ib, or a pharmaceutically acceptable salt, enantiomer of diastereomer thereof, wherein all of the above Provisos apply. Yet another embodiment of the present invention is a compound of Formula I, Ia, or Ib or a pharmaceutically acceptable salt, enantiomer of diastereomer thereof, wherein the above Provisos 2 and 9 apply. Yet another embodiment of the present invention is a compound of Formula I, Ia, or Ib or a pharmaceutically acceptable salt, enantiomer of diastereomer thereof, wherein the above Provisos 1, 4, 5, 6, 7 and 8 apply. Yet another embodiment of the present invention is a compound of Formula I, Ia, or Ib or a pharmaceutically acceptable salt, enantiomer of diastereomer thereof, wherein the above Provisos 1, 2, 4, 5, 6, 7, 8 and 9 apply. Yet another embodiment of the present invention is a compound of Formula I, Ia, or Ib or a pharmaceutically acceptable salt, enantiomer of diastereomer thereof, wherein the above Proviso 3 applies. Yet another embodiment of the present invention is a compound of Formula I, Ia, or Ib or a pharmaceutically acceptable salt, enantiomer of diastereomer thereof, wherein the above Provisos 2, 3, and 9 apply.

Another embodiment of the present invention is a pharmaceutical composition comprising: i) a compound of Formula I, Ia, or Ib, or a pharmaceutically acceptable salt, enantiomer of diastereomer thereof; and ii), a pharmaceutically acceptable carrier or diluent, wherein the above Provisos 2 and/or 9 apply.

Another embodiment of the present invention is a pharmaceutical composition comprising: i) a compound of Formulas I, Ia, or Ib, or a pharmaceutically acceptable salt, enantiomer of diastereomer thereof, and ii) a pharmaceutically acceptable carrier or diluent wherein Provisos 1, 4, 5, and 6 applies.

Another embodiment of the present invention is a pharmaceutical composition comprising: i) a compound of Formulas I, Ia, or Ib, or a pharmaceutically acceptable salt, enantiomer of diastereomer thereof; and ii) a pharmaceutically acceptable carrier or diluent; wherein Provisos 1, 2, 4, 5, 6 and 9 apply.

Another embodiment of the present invention is a pharmaceutical composition comprising: i) a compound of Formulas I, Ia, or Ib, or a pharmaceutically acceptable salt, enantiomer of diastereomer thereof, and ii) a pharmaceutically acceptable carrier or diluent; and wherein Proviso 3 applies.

Another embodiment of the present invention is a pharmaceutical composition comprising: i) a compound of Formulas I, Ia, or Ib, or a pharmaceutically acceptable salt, enantiomer of diastereomer thereof; and ii) a pharmaceutically acceptable carrier or diluent; wherein Provisos 1, 2, 3, 4, 5, 6 and 9 apply.

In another embodiment, Proviso 1 applies to the methods of treating a subject disclosed herein.

In another embodiment, Proviso 1 applies to the medical uses disclosed herein of a compound of Formulas I, Ia, or Ib, or a pharmaceutically acceptable salt, enantiomer or diastereomer thereof.

In another embodiment, Proviso 1 applies to the use of the compounds disclosed herein for the manufacture of a medicament.

In one embodiment, Proviso 1 applies when the subject is being treated to lower intraocular pressure.

In one embodiment, Proviso 1 applies when the subject is being treated for obesity or diabetes or depression.

DETAILED DESCRIPTION OF THE INVENTION

Specific values for the variables in the above-described Structural Formula I have the following values:

A is hydroxy($C_1$-$C_6$)alkyl or ($C_1$-$C_2$)alkoxy($C_1$-$C_6$)alkyl. Alternatively, A is ($C_1$-$C_4$)alkylcarbonylamino($C_1$-$C_4$)alkyl. In another embodiment, A is mono($C_1$-$C_2$)alkylaminocarbonyl($C_1$-$C_4$)alkyl or di($C_1$-$C_2$)alkylaminocarbonyl($C_1$-$C_4$)alkyl. In another embodiment, A is 2-pyrimidinyl-amino($C_1$-$C_6$)alkyl; 2-pyridyl-amino($C_1$-$C_6$)alkyl; mono($C_1$-$C_2$)alkylamino($C_1$-$C_4$)alkyl or di($C_1$-$C_2$)alkylamino($C_1$-$C_4$)alkyl, wherein the pyrimidinyl and pyridyl are each optionally substituted with methyl or ethyl. In another embodiment, A is ($C_1$-$C_6$)alkyl optionally substituted with halogen. In yet another embodiment, A is ($C_1$-$C_4$)alkylsulfonyl($C_1$-$C_4$)alkyl. Alternatively, A is ($C_1$-$C_4$)alkylsulfonylamino($C_1$-$C_4$)alkyl. In another embodiment, A is ($C_1$-$C_4$)alkoxyalkylamino($C_1$-$C_4$)alkyl. In another embodiment, A is mono($C_1$-$C_4$)alkylaminocarbonyl($C_1$-$C_4$)alkyl or di($C_1$-$C_4$)alkylaminocarbonyl($C_1$-$C_4$)alkyl.

$R^{1a}$ and $R^{1b}$ are H or ($C_1$-$C_6$)alkyl. Alternatively, $R^{1a}$ and $R^{1b}$ are H, methyl, or ethyl. In another embodiment, $R^{1a}$ is Me and $R^{1b}$ is H.

$R^2$ is optionally substituted aryl, optionally substituted heteroaryl or optionally substituted cycloalkyl. Alternatively, $R^2$ is optionally substituted phenyl, optionally substituted thienyl or optionally substituted pyridyl. In another embodiment, $R^2$ is optionally substituted phenyl. In yet another embodiment, E is a bond and $R^2$ is fluorophenyl.

$R^3$ is hydroxy($C_2$-$C_5$)alkyl. Alternatively, $R^3$ is ω-$H_2$NCO($C_1$-$C_3$)alkyl. In another embodiment, $R^3$ is MeS(=O)$_2$NH($C_2$-$C_4$)alkyl. In another embodiment $R^3$ is dihydroxy($C_3$-$C_5$)alkyl.

n is 0, 1, or 2. Alternatively, n is 1. In yet another embodiment, n is 0.

In a first specific embodiment, the variables for the Structural Formula I have the following values:

$R^3$ is selected from ($C_1$-$C_6$)alkyl, ($C_2$-$C_6$)alkenyl, ($C_2$-$C_6$)alkynyl; ($C_1$-$C_3$)alkoxy($C_2$-$C_3$)alkyl and ($C_2$-$C_3$)alkoxy($C_1$-$C_3$)alkyl wherein each is optionally substituted with up to four groups independently selected from cyano, $R^4$, HO; $R^4O_2C$—; $R^4S(=O)$—; $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and values and specific values for E, $R^2$, Y, n, Q, $R^{1a}$, $R^{1b}$, and A are described above.

In a second specific embodiment for Structural Formula I:

A is straight or branched ($C_1$-$C_8$)alkyl, ($C_2$-$C_8$)alkenyl or ($C_2$-$C_8$)alkynyl, optionally substituted with up to 4 groups independently selected from fluorine, cyano, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2$ NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, heterocyclylamino (wherein the heterocyclyl portion is optionally substituted by alkyl, haloalkyl or oxo); heteroarylamino (wherein the heteroaryl portion is optionally substituted by alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo); arylamino (wherein the aryl portion is optionally substituted by alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo); and cycloalkylamino (wherein the cycloalkyl portion is optionally substituted by alkyl, haloalkyl or oxo);

R$^3$ is as described for the first specific embodiment; and values and specific values for E, R$^2$, Y, n, Q, R$^{1a}$, R$^{1b}$, and A are described above.

Another embodiment is a compound of Formula Ia:

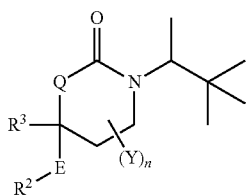

Ia wherein values and specific values for E, R$^2$, R$^3$, Q, Y and n are as defined for Formula I above.

Another embodiment is a compound of Formula Ib:

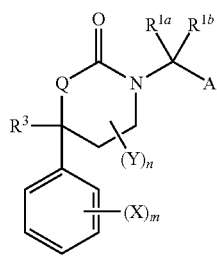

Ib wherein values and specific values for A, R$^{1a}$, R$^{1b}$, R$^3$, Q, Y and n are as defined for Formula I above, m is 0, 1, 2, 3 or 4 and substituents X are independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkylthio, (C$_4$-C$_7$)cycloalkylalkylthio, halo(C$_1$-C$_6$)alkylthio, halo(C$_3$-C$_6$)cycloalkylhio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkane-sulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cycloalkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkylamino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxy and (C$_1$-C$_6$)alkylcarbonyl.

Another embodiment is a compound of Formula I or any one of Formulas Ia-b wherein:

R$^{1a}$ is methyl or ethyl;
R$^{1b}$ is methyl or hydrogen;
A is methyl, ethyl, isopropyl or t-butyl;
n is 0;
E is a bond or CH$_2$;
R$^2$ is phenyl, thienyl or pyridyl each optionally substituted with halo or methyl; and
R$^3$ is methyl, ethyl, n-propyl, n-butyl, i-butyl, i-pentyl, vinyl or allyl each optionally substituted with up to two groups independently selected from HO—, MeO—, H$_2$N—, MeC(=O)NH—, MeS(=O)$_2$NH—, H$_2$NC(=O), MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O— oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC=N)NH—, or oxo;

or a pharmaceutically acceptable salt, enantiomer or diastereomer thereof.

Another embodiment is a compound of Formula I or any one of Formulas Ia-b wherein:
R$^{1a}$ is methyl;
R$^{1b}$ is hydrogen or methyl;
A is methyl or t-butyl;
n is 0;
E is a bond;
R$^2$ is phenyl or 4-fluorophenyl
R$^3$ is 2-hydroxethyl, 3-hydroxypropyl, 2,3-dihydroxypropyl, H$_2$NCOCH$_2$CH$_2$—, MeSO$_2$NHCH$_2$CH$_2$— or MeSO$_2$NHCH$_2$CH$_2$CH$_2$—;

or a pharmaceutically acceptable salt, enantiomer or diastereomer thereof.

DEFINITIONS

The term "alkyl", used alone or as part of a larger moiety such as "alkoxyalkyl" or "alkylamine" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, i-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl, cyclobutyl, cyclopentyl, cyclohexyl, cycloheptyl, cyclooctyl, bicyclo [2.2.2]octyl, bicyclo[2.2.1]heptyl, Spiro[4.4]nonane, adamantyl and the like. Unless otherwise described, exemplary substituents for a substituted cycloalkyl group include the substituents described for the cycloalkyl group represented by $R^2$.

The term "aryl" means an aromatic radical which is a phenyl group, a naphthyl group, an indanyl group or a tetrahydronaphthalene group. When substituted, an aryl group can be substituted with 1-4 substituents. Unless otherwise described, exemplary substituents for a substituted aryl group include the substituents described for the aryl group represented by $R^2$.

The term "heteroaryl" means a 5- and 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. When substituted, a heteroaryl group can be substituted with 1-4 substituents. Unless otherwise described, exemplary substituents for a substituted heteroaryl group include the substituents described for the heteroaryl group represented by $R^2$.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide. Unless otherwise described, exemplary substituents for a substituted heterocyclyl group include the substituents described for the heterocyclyl group represented by $R^2$.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "Si" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

The following abbreviations have the indicated meanings:

| Abbreviation | Meaning |
|---|---|
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| DAST | diethylaminosulfur trifluoride |
| DBU | 1,8-diazabicyclo[5.4.0]undec-7-ene |
| DCC | N,N'-dicyclohexylcarbodiimide |
| DCM | dichloromethane |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| EDC, EDC.HCl, EDCl | 1-[3-(dimethylamino)propyl]-3-ethylcarbodiimide hydrochloride |
| Equiv | equivalents |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| rt | room temperature |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| Tlc, TLC | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |

General Description of Synthetic Methods

Compounds of Formula I can be prepared by several processes. In the discussion below, A, E, Q, $R^{1a}$, $R^{1b}$, $R^3$, Y and n have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process a compound of Formula I, wherein Q is $NR^5$ can be prepared by reaction of diamine intermediate of Formula II with a reagent of Formula III, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at $-10°$ C. to $120°$ C.:

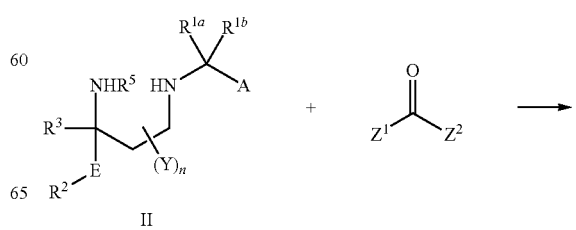

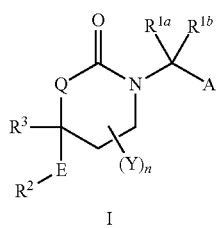

Certain instances of reagent III are especially convenient because they are commercially available. For example when $Z^1$ and $Z^2$ are both chloride, III is phosgene. When $Z^1$ and $Z^2$ are both 1-imidazolyl, III is carbonyl diimidazole. When $Z^1$ is chloride and $Z^2$ is p-nitrophenoxide, III is p-nitrophenyl chloroformate. When $Z^1$ and $Z^2$ are both $OCCl_3$, III is triphosgene and as little as one third of molar equivalent can be used.

Diamine intermediates of Formula IIa can be prepared by reduction of amides of Formula IV using a hydride reagent such as $BH_3$.THF solution, $BH_3$.$Me_2S$ or $LiAlH_4$ in an inert solvent ethereal such as THF or DME at 20° C. to 100° C. for between 1 h and 48 h:

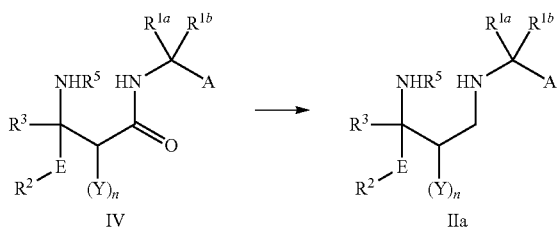

Aminoamide intermediates of Formula IV can be prepared by coupling of a β-aminoacid of Formula V with an amine of Formula VI using standard peptide coupling reagents such as EDC in the presence of HOBt and N,N-diisopropylethylamine in an inert solvent such as $CH_2Cl_2$ at 0-30° C. for between 1 h and 24 h:

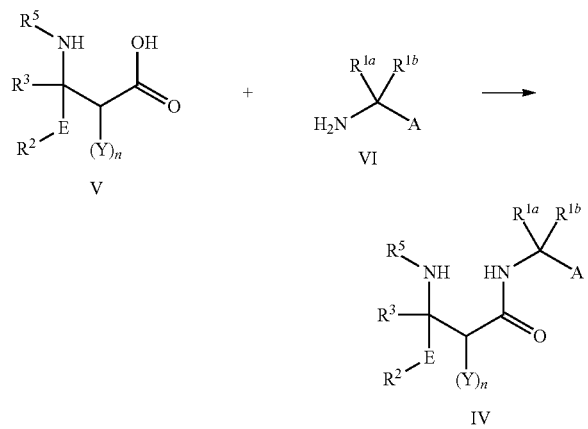

Methods for the synthesis β-aminoacids have been reviewed (Enantioselective Synthesis of β-Amino Acids (2nd Edition) (2005), Publisher: John Wiley & Sons, Inc., Hoboken, N.J.). One method for the synthesis of a compound of Formula V, wherein Y is $(C_1-C_6)$alkyl group, $R^5$ is H and n is 0, 1 or 2, is the addition of the enolate of an ester of Formula VIII, wherein $R^a$ is $(C_1-C_6)$alkyl and n is 0, 1 or 2, to a sulfinylimine of Formula VII to give a compound of Formula IX, followed by ester hydrolysis and removal of the t-butylsulfinyl group:

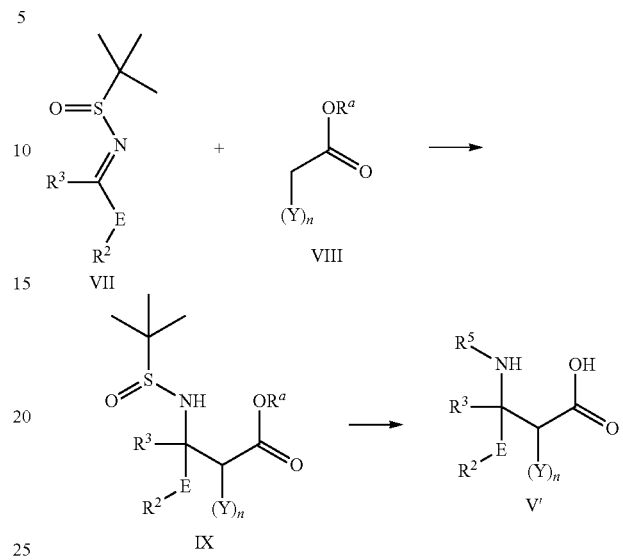

Amine intermediates of Formula VI, wherein $R^{1a}$ and $R^{1b}$ are both hydrogen, can be prepared by reduction of amides of Formula X using a hydride reagent such as $BH_3$.THF solution, $BH_3$.$Me_2S$ or $LiAlH_4$ in an inert solvent ethereal such as THF or DME at 20° C. to 100° C. for between 1 h and 48 h:

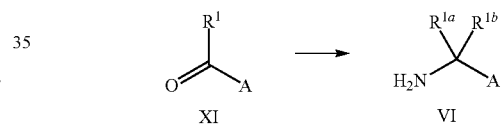

Amine intermediates of Formula VI, wherein $R^{1b}$ is hydrogen can be prepared from ketones and aldehydes of formula XI by reductive amination with ammonia or by reduction of oximes of Formula XII:

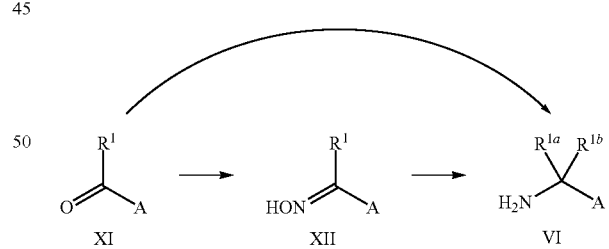

Methods for the conversion of ketones to oximes are described in Smith, M. B. and March, J. "March's Advanced Organic Chemistry" pp 1194-1195, 5th Edition, Wiley, New York, N.Y., 2001. Methods for the reduction of oximes to primary amines are described in Smith, M. B. and March, J. "March's Advanced Organic Chemistry" p 1555, 5th Edition, Wiley, New York, N.Y., 2001. Methods for the reductive amination of ketones are described in Baxter, E. W. and Reitz, A. B. "Organic Reactions" Volume 59, Ed. Overman, L. E., Wiley Interscience, 2002.

Intermediates of Formula II, wherein $R^{1a}$ and $R^{1b}$ are both hydrogen, can be prepared by reduction of amide intermediates of formula XIII using hydride reagents such as $BH_3$.THF solution, $BH_3$.$Me_2S$ or $LiAlH_4$ in an inert solvent ethereal such as THF or DME at 20° C. to 100° C. for between 1 h and 48 h:

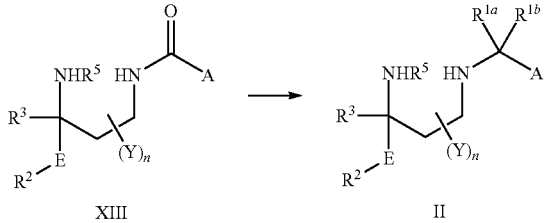

Amide intermediates of Formula XIII can be prepared by reaction of diamine intermediates of Formula XIV with activated carboxylic acids of Formula XV wherein $Z^3$ is chloride or an activated ester, such as an N-hydroxysuccinimide ester:

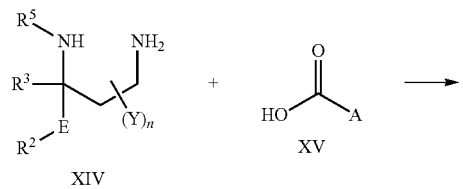

-continued

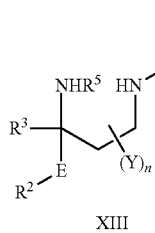

Diamine intermediates of Formula XIV, wherein n=0 and $R^5$=H, can be prepared by reaction of an aziridines of Formula XVI, wherein $R^b$ is a suitable amine protecting group such as t-butoxycarbonyl, with cyanide ion followed by deprotection to give β-aminonitriles of Formula XVII followed by reduction with hydrogen gas in the presence of a catalyst or with a hydride source such as $LiAlH_4$:

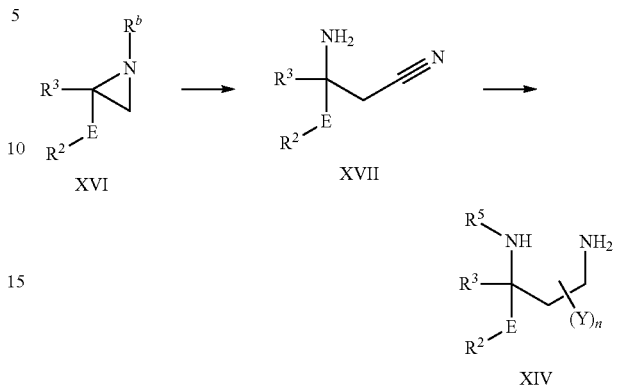

Diamine intermediates of Formula XIV, wherein n is 0, can be prepared by treatment of sulfonate intermediates of Formula XIX, wherein $R^c$ is for example methyl, trifluoromethyl or p-methylphenyl, with (i) ammonia or (ii) with $NaN_3$ followed by reduction using $PPh_3$ in wet THF or $H_2$ gas and a palladium catalyst:

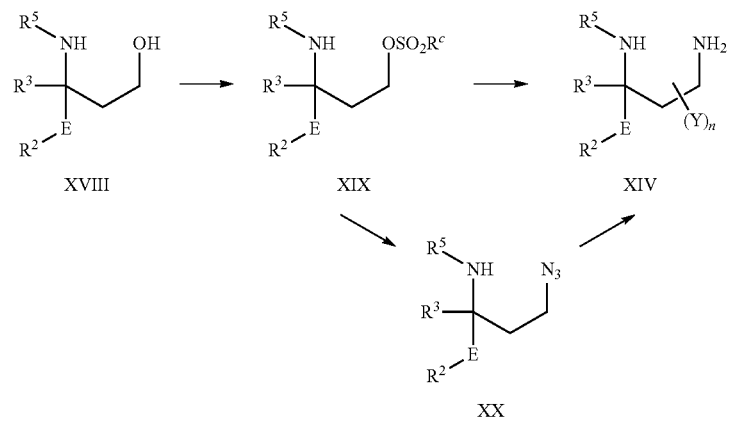

Sulfonate intermediates of Formula XIX are prepared by reaction of, preferably N-protected, alcohol intermediates Formula XVIII with $R^cSO_2Cl$ or $(R^cSO_2)_2O$. In addition sulfonate intermediates of Formula XIX can be reacted with amines of Formula VI to afford diamine intermediates of Formula II:

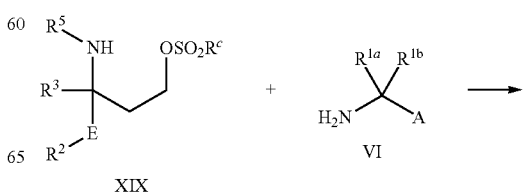

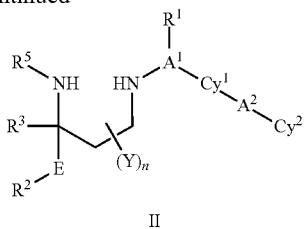

II

Aminoalcohol intermediates of Formula XVIII can be prepared by hydroboration of allylic amines of Formula XXI:

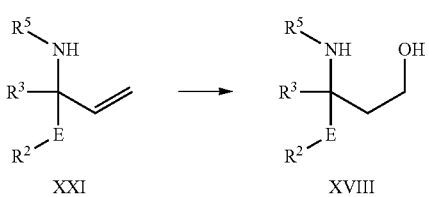

Diamine intermediates of Formula II, wherein $R^{1b}$ is hydrogen can be prepared by reaction of, preferably protected, diamines of Formula XIV with aldehydes or methyl ketones of Formula XXII in the presence of a reducing agent such as $NaCNBH_3$ or $Na(OAc)_3BH$:

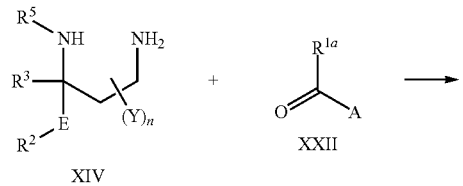

Methods for the reductive amination of aldehydes and ketones are described in Baxter, E. W. and Reitz, A. B. "Organic Reactions" Volume 59, Ed. Overman, L. E., Wiley Interscience, 2002.

In a second process a compound of Formula I can be prepared by treatment of an aminocarbamate ($Q=NR^5$) or hydroxycarbamate ($Q=O$) of Formula XXIII, wherein $R^d$ is an alkyl or arylalkyl group such as methyl, t-butyl or benzyl, with a strong base such as sodium hydride:

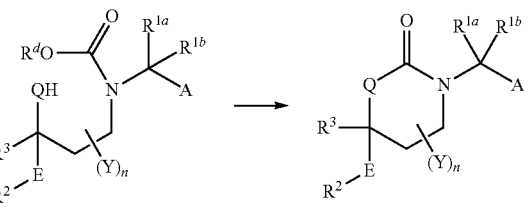

Aminocarbamates of Formula XXIII, wherein Q is $NR^5$ and $R^5$ is H, can be prepared by reaction of iminocarbamates of Formula XXIV, wherein $R^d$ is an alkyl or arylalkyl group such as methyl, t-butyl or benzyl, with organometallic reagents of Formula XXV, wherein M is Li, MgCl, MgBr and MgI, followed by removal of the t-butylsulfinyl group:

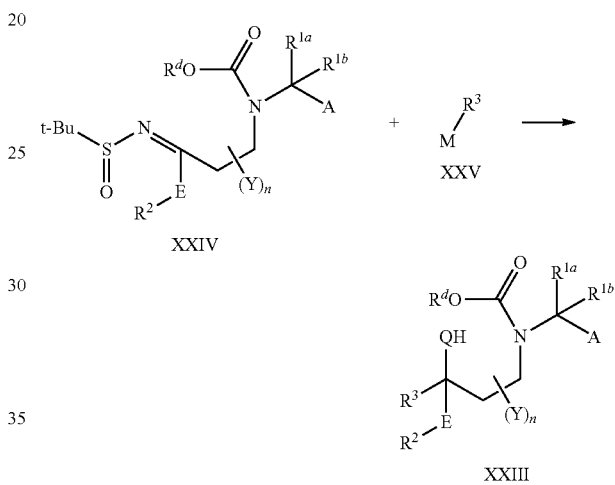

Iminocarbamates of Formula XXIV can be prepared by reaction of ketocarbamates of Formula XXVI with 2-methylpropane-2-sulfinamide:

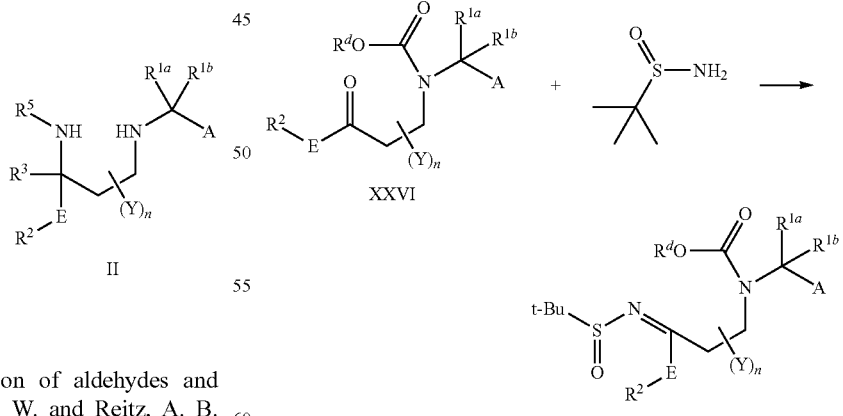

Ketocarbamates of Formula XXVI can be prepared by reaction of aminoketones of Formula XXVII with intermediates of Formula XVIII wherein $R^e$ is a leaving group such as chloride, succinyloxy, imidazolyl or t-butoxycarboxycarbonyl:

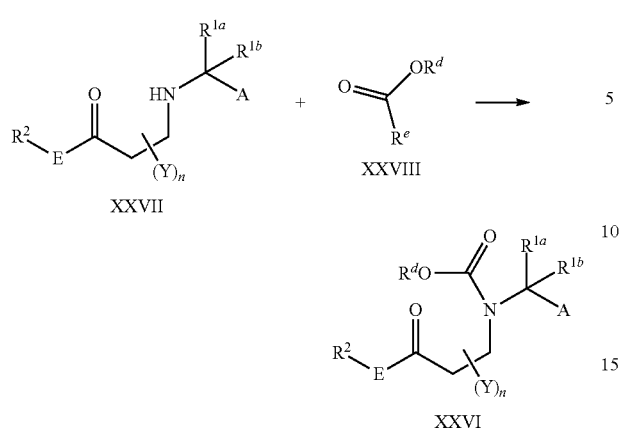

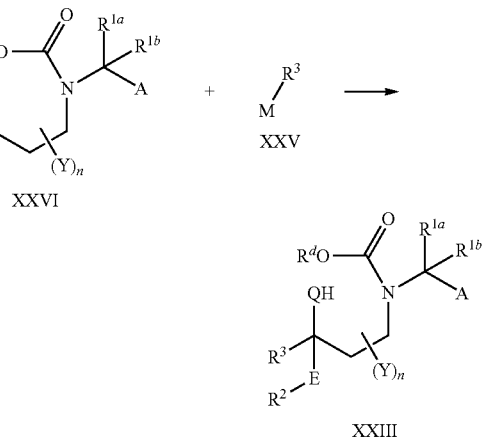

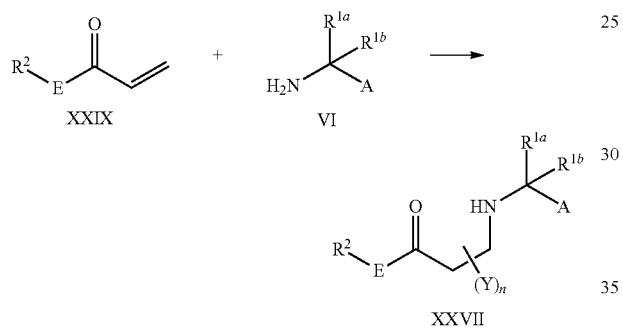

Aminoketones of Formula XXVII, wherein n=0, can be prepared by reaction of α,β-unsaturated ketones of Formula XXIX with amines of Formula VI:

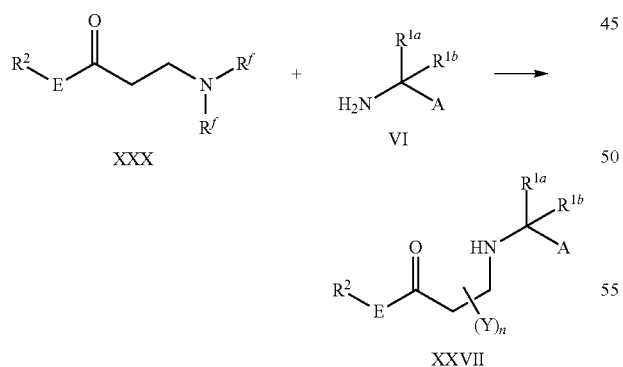

Aminoketones of Formula XXVII, wherein n=0, can also be prepared by reaction of β-dialkylaminoketones of Formula XXX, wherein $R^f$ is lower alkyl especially methyl, with amines of Formula VI:

β-Dialkylaminoketones of Formula XXXII are in turn derived from α,β-unsaturated ketones of Formula XXIX with dialkylamines of Formula $R^fNHR^f$.

Hydroxycarbamates (Q=O) of Formula XXIII can be prepared by reaction of ketones of Formula XXVI with organometallics of Formula XXV wherein M=MgCl, MgBr, MgI or Li Hydroxycarbamates (Q=O) of Formula XXIII can also be prepared by reaction of aminoalcohols of Formula XXXI with an acylating agent of Formula XXVIII:

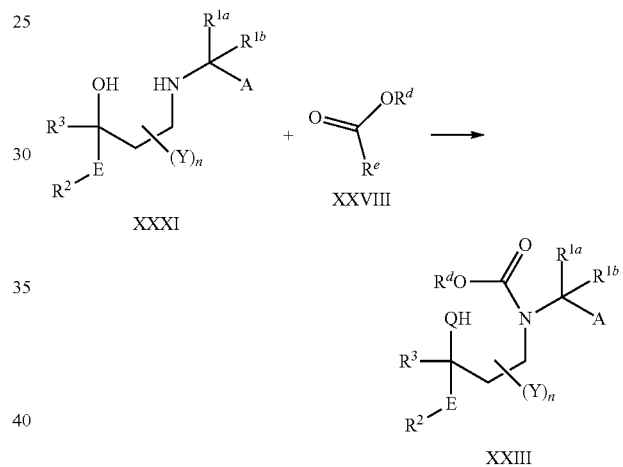

Aminoalcohols of Formula XXXI can be prepared by addition of an organometallic reagent of Formula XXV to an aminoketone of Formula XXIX.

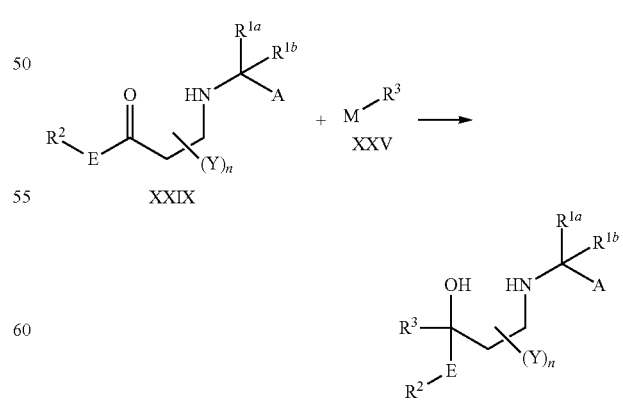

Intermediates of Formula XXXI, wherein n=0, can be prepared by reaction of oxetanes of Formula XXXII with amines of Formula VI as described in Smith, M. B. and March, J. "March's Advanced Organic Chemistry" p 505, 5th Edition, Wiley, New York, N.Y., 2001:

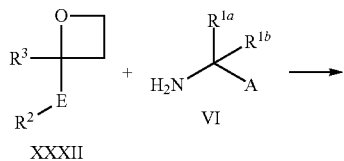
XXXII

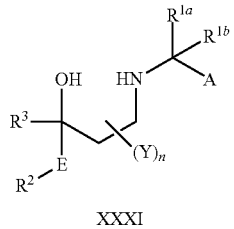
XXXI

Aminoalcohol intermediates of Formula XXXI can be prepared by reduction of amides of Formula XXXIII using a hydride reagent such as $BH_3$.THF solution, $BH_3$.$Me_2S$ or $LiAlH_4$ in an inert solvent ethereal such as THF or DME at 20° C. to 100° C. for between 1 h and 48 h:

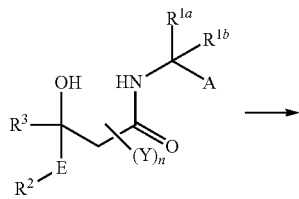
XXXIII

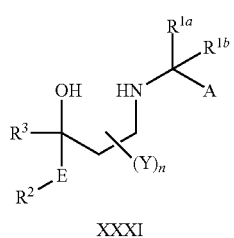
XXXI

Intermediates of Formula XXXIII can be prepared by coupling of β-hydroxyacids of Formula XXXIV with an amines of Formula VI using standard peptide coupling reagents such as EDC in the presence of HOBt and N,N-diisopropylethylamine in an inert solvent such as $CH_2Cl_2$ at 0-30° C. for between 1 h and 24 h:

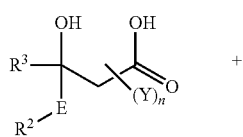
XXXIV

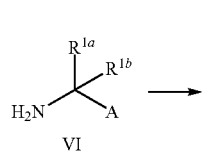
VI

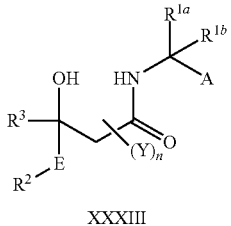
XXXIII

Intermediates of Formula XXXIII, wherein $R^{1a}$ and $R^{1b}$ are both hydrogen, can be prepared by reduction of amide intermediates of formula XXXV using a hydride reagent such as $BH_3$.THF solution, $BH_3$.$Me_2S$ or $LiAlH_4$ in an inert solvent ethereal such as THF or DME at 20° C. to 100° C. for between 1 h and 48 h:

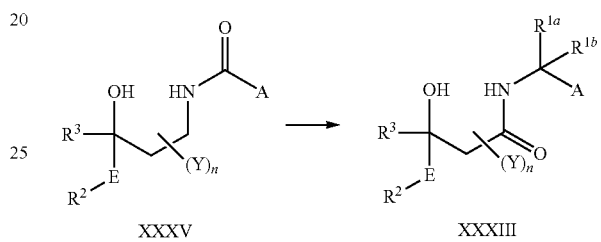
XXXV                XXXIII

Amide intermediates of Formula XXXV can be prepared by reaction of an amino-alcohol intermediate of Formula XXXVI with a carboxylic acid of Formula XV using standard peptide coupling conditions, such as EDC in the presence of HOBt:

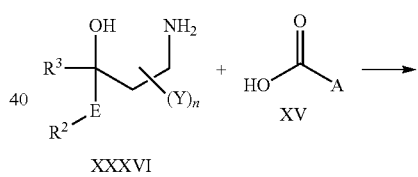
XXXVI         XV

XXXV

Amino-alcohol intermediates of Formula XXXVI, wherein n=0, can be prepared by reaction of an epoxide of Formula XXXVII with cyanide ion followed by reduction of the resulting hydroxynitrile of Formula XXXVIII with hydrogen gas in the presence of a catalyst or with a hydride source such as $LiAlH_4$:

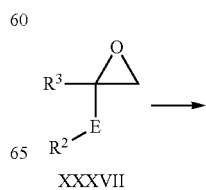
XXXVII

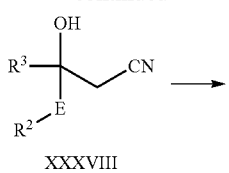

XXXVIII

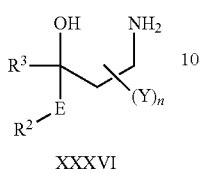

XXXVI

Epoxide compounds of formula XIV can, in turn, be prepared in a number of ways including, as described in Aube, J. "Epoxidation and Related Processes" Chapter 3.2 in Volume 1 of "Comprehensive Organic Synthesis" Edited by B. M. Trost, I. Fleming and Stuart L. Schreiber, Pergamon Press, New York, 1992.

Hydroxynitrile intermediates of Formula XXXVIII can be prepared by treatment of ketones of Formula XXXIX with acetonitrile anion, formed by treatment of acetonitrile with n-BuLi or LDA, in an inert, anhydrous solvent such as THF at low temperature:

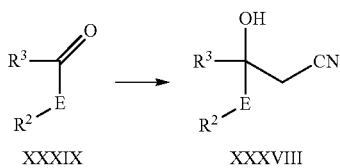

XXXIX    XXXVIII

Amino-alcohol intermediates of Formula XXXVI, wherein n is 0, can be prepared by treatment of sulfonate intermediates of Formula XL, wherein $R^A$ is for example methyl, trifluoromethyl or p-methylphenyl, with ammonia:

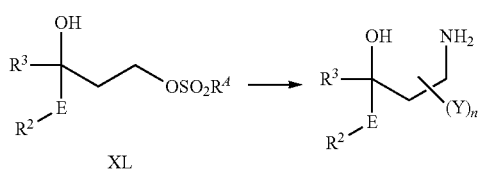

XL    XXXVI

Amino-alcohol intermediates of Formula XXXVI can be prepared by treatment of sulfonate intermediates of Formula XL with sodium azide to give an azide intermediate of Formula XLI, followed by catalytic hydrogenation or by Staudinger reduction with $PPh_3$ in wet THF:

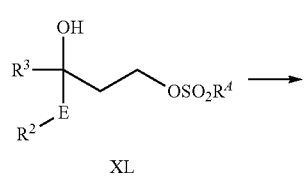

XL

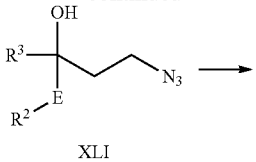

XLI

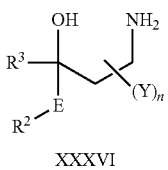

XXXVI

Sulfonate intermediates of Formula XL can be prepared from diol intermediates of Formula XLII with a sulfonyl chloride $R^4SO_2Cl$:

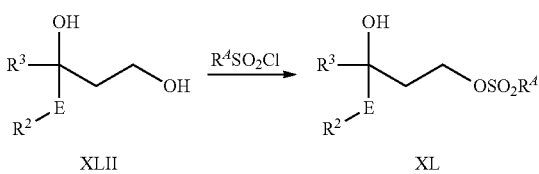

XLII    XL

Diol intermediates of Formula XLII can be prepared by hydroboration of allyl alcohols of Formula XLIII:

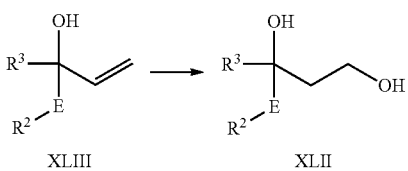

XLIII    XLII

Diol intermediates of Formula XLI can be prepared by ozonolysis and reduction of homoallyl alcohols of Formula XLIV:

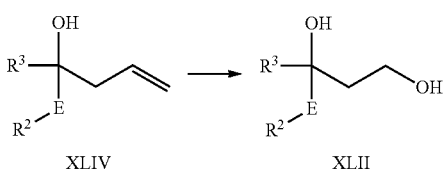

XLIV    XLII

Aminoalcohol intermediates of Formula XXXI, wherein $R^{1b}$ is hydrogen, can be prepared by reaction of an aminoalcohol of Formula XXXVI with an aldehyde or methyl ketone of Formula XXII in the presence of a reducing agent such as $NaCNBH_3$ or $Na(OAc)_3BH$:

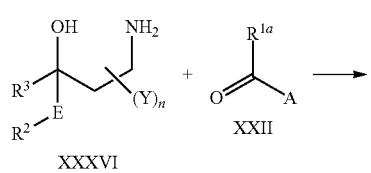

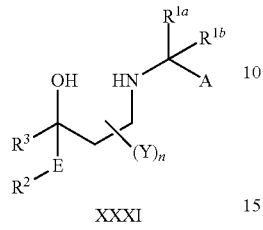

Methods for the reductive amination of aldehydes and ketones are described in Baxter, E. W. and Reitz, A. B. "Organic Reactions" Volume 59, Ed. Overman, L. E., Wiley Interscience, 2002.

Aminoalcohols of Formula XXXI can be prepared by nucleophilic substitution of sulfonates of Formula XL or halides of Formula XLV with amines of Formula VI:

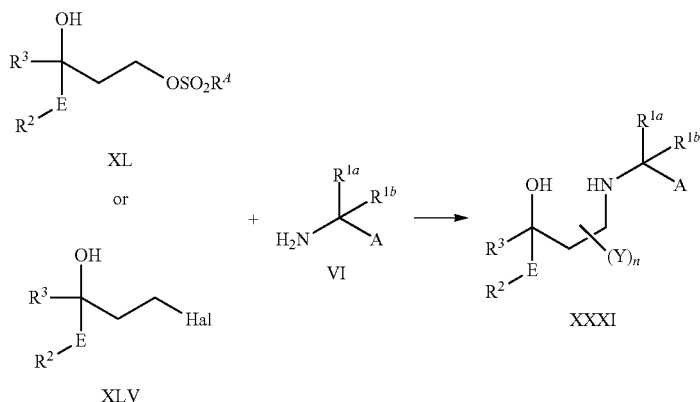

In a third process a compound of Formula I, wherein $R^{1a}$ and $R^{1b}$ are both hydrogen, can be prepared by reaction of a compound of Formula XLVI, with a compound of Formula XLVII, wherein $R^9$ is a leaving group such as Br, I, $OSO_2Me$, $OSO_2CF_3$ or $OSO_2Ph$, in the presence of a base such as NaH or $K_2CO_3$:

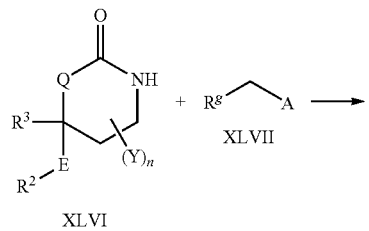

Compounds of Formula XLVI can be prepared by treatment of compounds of Formula XIV and XXXVI with various reagents of Formula III, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at $-10°$ C. to $120°$ C.:

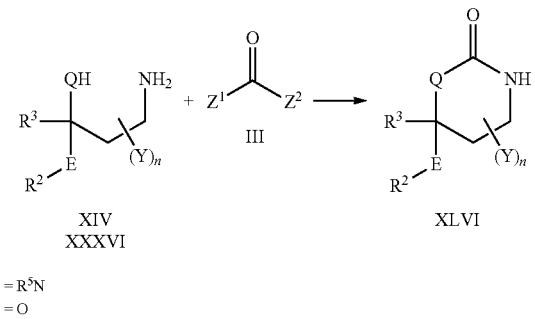

$Q = R^5N$
$Q = O$

In a fourth process a compound of Formula I wherein Q is O and n is 0, can be prepared by reaction of a halo compound of Formula XLV, wherein Hal is chlorine or bromine, with an isocyanate of Formula XLVIII in the presence of a base:

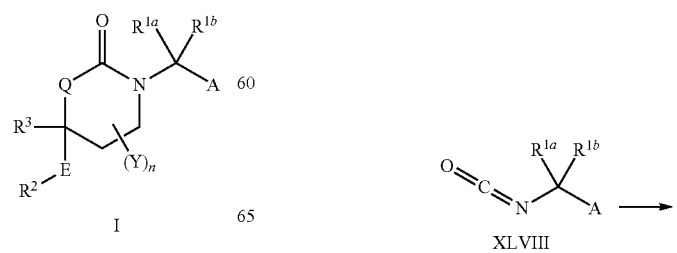

-continued

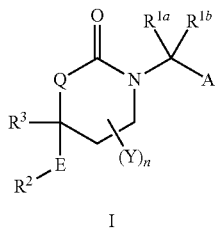

I

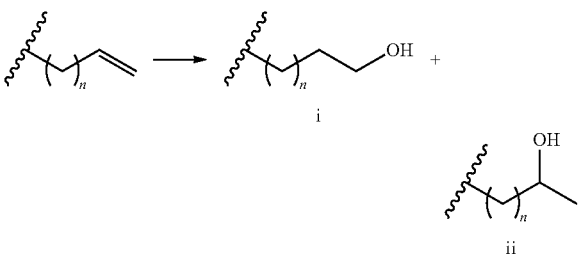

n = 0-4

Halo compounds of Formula XLV can be prepared by reaction of β-haloketones of Formula XLIX with organometallic reagents of Formula XXV wherein M is a metal containing radical including MgCl, MgBr, MgI or Li. The reaction is optionally carried out in the presence of anhydrous cerium trichloride:

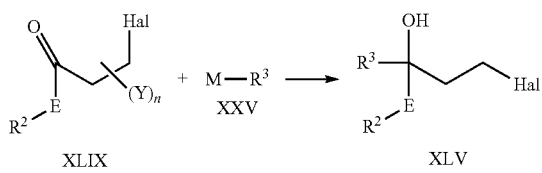

In a fifth process a compound of Formula I can be prepared from another compound of Formula I. For example:

(1) a compound of Formula I wherein $R^2$ is aryl or heteroaryl substituted with bromine or iodine, can be reacted with Cu(I)CN or with Zn(CN)2 in the presence of a palladium catalyst to give a compound of Formula I wherein $R^2$ is aryl or heteroaryl substituted with cyano.

(2) a compound of Formula I wherein A or $R^3$ is ω-hydroxy($C_2$-$C_6$)alkyl can be oxidized to a compound of Formula I wherein A or $R^3$ is ω-carboxy($C_1$-$C_5$)alkyl using Jones reagent.

(3) a compound of Formula I wherein A or $R^3$ is ω-carboxy($C_1$-$C_6$)alkyl can be coupled with ammonia or a ($C_1$-$C_6$)alkylamine using a standard peptide coupling reagent such as EDC to afford a compound of Formula I wherein A or $R^3$ is ω-$H_2NC(=O)(C_1$-$C_6$)alkyl or • or ω-{($C_1$-$C_6$)alkylNHC(=O)}($C_1$-$C_6$)alkyl.

(4) a compound of Formula I wherein A or $R^3$ is ω-hydroxy($C_1$-$C_6$)alkyl can be converted to its methanesulfonate or trifluoromethanesulfonate, treated with sodium azide and reduced to give a compound of Formula I, wherein A or $R^3$ is ω-amino($C_1$-$C_6$)alkyl.

(5) a compound of Formula I wherein A or $R^3$ is amino($C_1$-$C_6$)alkyl can be reacted with acetic anhydride or acetyl chloride to give a compound of Formula I wherein A or $R^3$ is {acetylamino}($C_1$-$C_6$)alkyl.

(6) a compound of Formula I wherein A or $R^3$ is amino($C_1$-$C_6$)alkyl can be reacted with methanesulfonyl chloride to give a compound of Formula I wherein A or $R^3$ is {methanesulfonylamino}($C_1$-$C_6$)alkyl.

(7) a compound of Formula I, wherein A or $R^3$ is ($C_2$-$C_6$) alkenyl is hydroborated to afford a compound of Formula I wherein A or $R^3$ is hydroxy($C_2$-$C_6$)alkyl. When the alkene is at the terminus of the ($C_2$-$C_6$)alkenyl group, the major product is generally the primary ω-hydroxy($C_2$-$C_6$)alkenyl i and the minor product is the secondary alcohol ii.

(8) a compound of Formula I, wherein A or $R^3$ is ($C_2$-$C_6$) alkenyl, can be reacted with osmium tetroxide and N-methylmorpholine-N-oxide to afford a compound of Formula I wherein A or $R^3$ is vicinal dihydroxy($C_2$-$C_6$)alkyl, (9) a compound of Formula I, wherein A or $R^3$ is ($C_2$-$C_6$) alkenyl, can be reacted with ozone followed by $NaBH_4$ to give a compound of Formula I wherein A or $R^3$ is ω-hydroxy($C_1$-$C_5$)alkyl.

(10) a compound of Formula I wherein A or $R^3$ is amino ($C_1$-$C_6$)alkyl can be reacted with an ($C_1$-$C_6$)alkyl isocyanate to give a compound of Formula I wherein A or $R^3$ is ($C_1$-$C_6$) alkylaminocarbonylamino($C_1$-$C_6$)alkyl.

(11) a compound of Formula I wherein A or $R^3$ is amino ($C_1$-$C_6$)alkyl can be reacted with an ($C_1$-$C_6$)alkyl chloroformate to give a compound of Formula I wherein A or $R^3$ is ($C_1$-$C_6$)alkoxycarbonylamino($C_1$-$C_6$)alkyl.

(12) a compound of Formula I wherein A or $R^3$ is amino ($C_1$-$C_6$)alkyl can be reacted with chlorosulfonyl isocyanate or sulfamide to give a compound of Formula I wherein A or $R^3$ is aminosulfonylamino($C_1$-$C_6$)alkyl.

(13) a compound of Formula I wherein A or $R^3$ is amino ($C_1$-$C_6$)alkyl can be reacted with a ($C_1$-$C_6$)alkylsulfamoyl chloride to give a compound of Formula I wherein A or $R^3$ is ($C_1$-$C_6$)alkylaminosulfonylamino($C_1$-$C_6$)alkyl.

(14) a compound of Formula I wherein A or $R^3$ is hydroxy ($C_1$-$C_6$)alkyl can be reacted with chlorosulfonyl isocyanate to give a compound of Formula I wherein A or $R^3$ is aminosulfonyloxy($C_1$-$C_6$)alkyl.

(15) a compound of Formula I wherein A or $R^3$ is hydroxy ($C_1$-$C_6$)alkyl can be reacted with p-nitrophenyl chloroformate, pentafluorophenyl chloroformate or carbonyl diimidazole, followed by ammonia, a ($C_1$-$C_6$)alkylamine or a di($C_1$-$C_6$)alkylamine to give a compound of Formula I wherein A or $R^3$ is aminocarboxy($C_1$-$C_6$)alkyl, ($C_1$-$C_6$)alkyl aminocarboxy($C_1$-$C_6$)alkyl or di($C_1$-$C_6$)alkylaminocarboxy($C_1$-$C_6$) alkyl.

(16) a compound of Formula I wherein A or $R^3$ is hydroxy ($C_1$-$C_6$)alkyl can be reacted with $POCl_3$ to give a compound of Formula I wherein A or $R^3$ is $(HO)_2P(=O)O(C_1$-$C_6$)alkyl.

(17) a compound of Formula I wherein Q is $NR^5$ and $R^5$ is H, can be reacted with an ($C_1$-$C_6$)alkyl halide in the presence of a strong base such as sodium hydride to afford a compound of Formula I wherein $R^5$ is ($C_1$-$C_6$)alkyl.

(18) a compound of Formula I wherein A or $R^3$ is ω-$H_2NCO(C_1$-$C_5$)alkyl can be reacted with TFAA in the presence of pyridine to afford a compound of Formula I wherein A or $R^3$ is ω-cyano($C_1$-$C_6$)alkyl.

(19) a compound of Formula I wherein A or $R^3$ is hydroxy ($C_1$-$C_6$)alkyl can be reacted with an ($C_1$-$C_6$)alkyl halide in the presence of a strong base such sodium hydride to give a compound of Formula I wherein A or R3 is ($C_1$-$C_6$)alkoxy ($C_1$-$C_6$)alkyl.

(20) a compound of Formula I wherein A or $R^3$ is hydroxy($C_1$-$C_6$)alkyl can be reacted with an ($C_3$-$C_6$)alkenyl halide in the presence of a strong base such sodium hydride followed by hydroboration to give a compound of Formula I wherein A or $R^3$ is hydroxy($C_3$-$C_6$)alkoxy($C_1$-$C_6$)alkyl.

(21) a compound of Formula I wherein A or $R^3$ is hydroxy($C_1$-$C_6$)alkyl can be reacted with an ($C_3$-$C_6$)alkenyl halide in the presence of a strong base such sodium hydride followed by treatment with ozone and $NaBH_4$ to give a compound of Formula I wherein A or $R^3$ is hydroxy($C_2$-$C_6$)alkoxy($C_1$-$C_6$)alkyl.

(22) a compound of Formula I wherein A or $R^3$ is ω-hydroxy($C_1$-$C_6$)alkyl can be converted to its methanesulfonate or trifluoromethanesulfonate, treated with a ($C_1$-$C_6$)alkylamine or di($C_1$-$C_6$)alkylamine to give a compound of Formula I wherein A or $R^3$ is ($C_1$-$C_6$)alkylamino($C_1$-$C_6$)alkyl or di($C_1$-$C_6$)alkylamino($C_1$-$C_6$)alkyl.

(23) a compound of Formula I wherein A or $R^3$ is amino($C_1$-$C_6$)alkyl can be reacted with a trifluoroacetic anhydride followed by reduction with BH3.THF to give a compound of Formula I wherein A or $R^3$ is 2,2,2-trifluoroethylamino($C_1$-$C_6$)alkyl.

(24) a compound of Formula I wherein A or $R^3$ is amino($C_1$-$C_6$)alkyl can be reacted with a 2-fluoropyridine to give a compound of Formula I wherein A or $R^3$ is 2-pyridylamino($C_1$-$C_6$)alkyl.

(25) a compound of Formula I wherein A or $R^3$ is ω-hydroxy($C_1$-$C_6$)alkyl can be converted to its methanesulfonate or trifluoromethanesulfonate, treated with a ($C_1$-$C_6$)alkylthiol followed by oxidation with m-CPBA to give a compound of Formula I wherein A or $R^3$ is ($C_1$-$C_6$)alkylsulfonyl($C_1$-$C_6$)alkyl.

(26) a compound of Formula I wherein A or $R^3$ is ω-hydroxy($C_1$-$C_6$)alkyl can be treated with isobutylene in the presence of acid to give a compound of Formula I wherein A or $R^3$ is ω-t-butoxy($C_1$-$C_6$)alkyl.

(27) a compound of Formula I wherein A is $CO_2Me$ or $CH_2CO_2Me$ can be treated with MeMgBr to afford a compound of Formula I wherein A is $CMe_2OH$ or $CH_2CMe_2OH$.

Purification Methods

Compounds of the invention can be purified by high pressure liquid chromatography (prep HPLC). Unless otherwise specified, prep HPLC refers to preparative reverse phase HPLC on a C-18 column eluted with a water/acetonitrile gradient containing 0.01% TFA run on a Gilson 215 system.

LC-MS Methods

Method 1 (30-90)

| Column | YMC-PACK ODS-AQ, 50 × 2.0 mm 5 μm | | |
|---|---|---|---|
| Mobile Phase | A: water (4 L) + TFA (1.5 mL)) | | |
| | B: acetonitrile (4 L) + TFA (0.75 mL)) | | |
| | TIME(min) | A % | B % |
| | 0 | 70 | 30 |
| | 2.2 | 10 | 90 |
| | 2.5 | 10 | 90 |
| Flow Rate | 1 mL/min | | |
| Wavelength | UV220 | | |
| Oven Temp | 50° C. | | |
| MS ionization | ESI | | |

Method 2 (10-80)

| Column | YMC-PACK ODS-AQ, 50 × 2.0 mm 5 μm | | |
|---|---|---|---|
| Mobile Phase | A: water (4 L) + TFA (1.5 mL)) | | |
| | B: acetonitrile (4 L) + TFA (0.75 mL)) | | |
| | TIME(min) | A % | B % |
| | 0 | 90 | 10 |
| | 2.2 | 20 | 80 |
| | 2.5 | 20 | 80 |
| Flow Rate | 1 mL/min | | |
| Wavelength | UV 220 nm | | |
| Oven Temp | 50° C. | | |
| MS ionization | ESI | | |

EXAMPLE 1

3-((2S)-3,3-dimethylbutan-2-yl)-6-(4-fluorophenyl)-6-(2-hydroxyethyl)-1,3-oxazinan-2-one

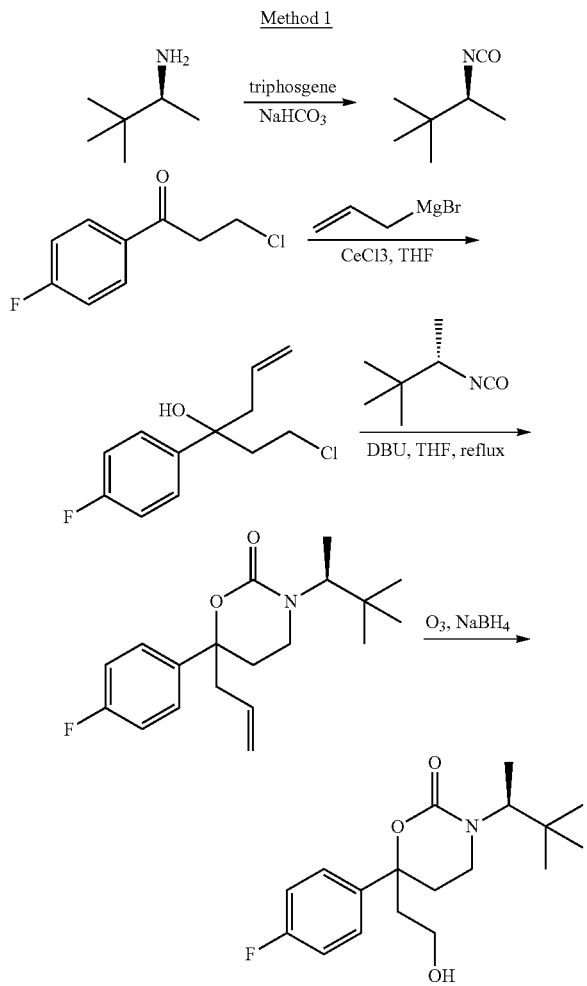

Method 1

Step 1

To a solution of (S)-1,2,2-trimethylpropylamine (626 mg, 6.2 mmol) in methylene chloride (20 mL) and satd aq $NaHCO_3$ (20 mL) was added triphosgene (607 mg, 2.05 mmol) at 0° C. The mixture was stirred for 15 min. The organic phase was separated, dried and concentrated to give (S)-3-isocyanato-2,2-dimethyl-butane (845 mg, 90%). $^1$H NMR (CDCl$_3$): 0.90 (s, 9H), 1.21 (m, 3H), 3.31 (m, 1H).

Step 2

A 1000-mL flask was charged with anhydrous CeCl$_3$ (50 g, 0.2 mol) and THF (360 mL). The mixture was vigorously stirred for 3.5 h at rt. The suspension was then cooled to −78° C., and a solution of allylmagnesium bromide (1.0 M in THF, 188.2 mL, 188 mmol) was added. After stirring for 2 h at −78° C., a solution of 3-chloro-1-(4-fluorophenyl)propan-1-one (22.6 g, 120 mmol) in THF (269 mL) was added dropwise. The reaction mixture was allowed to slowly warm to rt while stirring overnight. The reaction was then quenched with satd aq NaHCO$_3$, extracted with EtOAc and dried over Na$_2$SO$_4$. After the solvents were evaporated, the residue was purified by chromatography on silica gel eluted with hexanes/EtOAc to afford of 1-chloro-3-(4-fluorophenyl)hex-5-en-3-ol (23.8 g, 87%) as an oil. $^1$H NMR (CDCl$_3$): 2.27 (m, 1H), 2.31 (m, 2H), 2.50 (m, 1H), 2.69 (m, 1H), 3.19 (m, 1H), 3.52 (m, 1H), 5.16 (m, 2H), 5.51 (m, 1H), 7.04 (m, 2H), 7.35 (m, 2H).

Step 3

A mixture of 1-chloro-3-(4-fluorophenyl)hex-5-en-3-ol (500 mg, 2.19 mmol), (S)-3-isocyanato-2,2-dimethyl-butane (845 mg, 5.58 mmol), and DBU (681 mg, 5.9 mmol) in THF (10 mL) was heated to reflux for 25 h. The mixture was diluted with EtOAc and washed with 1 N aq HCl. The aqueous phase was extracted with EtOAc (3×). The combined organic phase was dried over Na$_2$SO$_4$. After the solvents were evaporated, the crude product was purified by column to give 6-allyl-3-((2S)-3,3-dimethylbutan-2-yl)-6-(4-fluorophenyl)-1,3-oxazinan-2-one (80 mg, crude).

Step 4

A solution of 6-allyl-3-((S)-3,3-dimethylbutan-2-yl)-6-(4-fluorophenyl)-1,3-oxazinan-2-one (80 mg, crude) in dry CH$_2$Cl$_2$ (5 mL) was treated with ozone at −78° C. until the mixture turned blue. The system was then flushed with oxygen to move excess ozone. NaBH$_4$ (47 mg, 1.25 mmol) was added to the mixture in portions at rt. The mixture was stirred overnight at rt. The mixture was quenched with water and the layers were separated. The aqueous layer was extracted with CH$_2$Cl$_2$ (2×6 mL). The organic layer was combined, washed with brine, dried over anhydrous Na$_2$SO$_4$ and concentrated to give the crude product, which was purified by preparative TLC to give 3-((2S)-3,3-dimethylbutan-2-yl)-6-(4-fluorophenyl)-6-(2-hydroxyethyl)-1,3-oxazinan-2-one (5 mg, yield: 4%).

Method 2

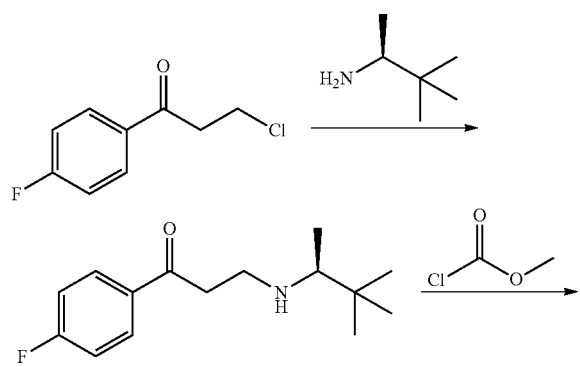

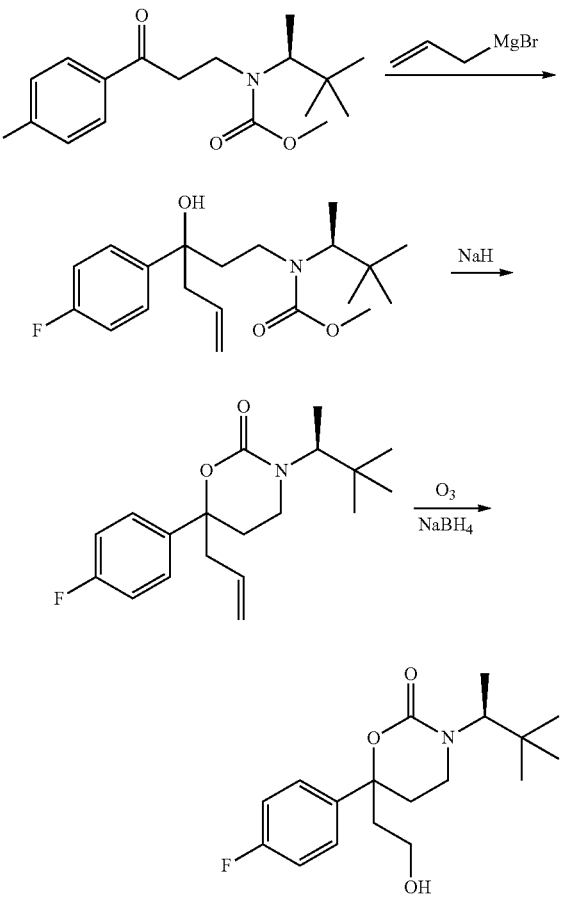

Step 1

To a solution of 3-chloro-1-(4-fluorophenyl)propan-1-one (5.0 g, 0.027 mol) and K$_2$CO$_3$ (7.45 g, 0.054 mol) in acetonitrile (100 mL) was added (S)-3,3-dimethylbutan-2-amine (3.24 g, 0.032 mol), and the reaction mixture was stirred at rt overnight. The solution was filtered, and the filtrate was concentrated to give (S)-3-(3,3-dimethylbutan-2-ylamino)-1-(4-fluorophenyl)propan-1-one (6.40 g, 94%). $^1$H NMR (CDCl$_3$): 0.82 (s, 9H), 0.91-0.96 (d, 3H), 2.14-2.22 (m, 1H), 2.73-2.82 (m, 1H), 3.01-3.11 (m, 3H), 7.01-7.09 (m, 2H), 7.88-7.96 (m, 2H).

Step 2

To a solution of (S)-3-(3,3-dimethylbutan-2-ylamino)-1-(4-fluorophenyl)propan-1-one (2.00 g, 7.97 mmol) and K$_2$CO$_3$ (3.30 g, 23.9 mmol) in CH$_2$Cl$_2$ (100 mL) was added methyl chloroformate (2.25 g, 23.9 mmol) dropwise at 0° C., and the reaction mixture was stirred at rt overnight. The solution was filtered, and the filtrate was concentrated to give the crude product, which was purified by chromatography to afford (S)-methyl 3,3-dimethylbutan-2-yl(3-(4-fluorophenyl)-3-oxopropyl)carbamate (2.0 g, 81%). $^1$H NMR (CDCl$_3$): 0.92 (s, 9H), 1.12-1.21 (d, 3H), 3.02-3.11 (m, 1H), 3.27-3.49 (m, 1H), 3.66 (s, 3H), 3.98-4.23 (m, 1H), 7.06-7.17 (m, 2H), 7.92-8.08 (m, 2H).

Step 3

To a solution of (S)-methyl 3,3-dimethylbutan-2-yl(3-(4-fluorophenyl)-3-oxopropyl)carbamate (4.5 g, 0.015 mol) in THF (60 mL) was added allymagnesium bromide (1 M, 30 mL, 0.03 mol) dropwise at −78° C. under $N_2$. After adding completely, the reaction mixture was stirred at rt overnight. The reaction was quenched with saturated aqueous $NH_4Cl$ solution, and the mixture was extracted with EtOAc. The combined organic layer was washed with brine, dried over $Na_2SO_4$, filtered and concentrated to give methyl (S)-3,3-dimethylbutan-2-yl(3-(4-fluorophenyl)-3-hydroxyhex-5-enyl)carbamate (4.80 g, 92%), which was used for the next step without further purification.

Step 4

To a solution of (S)-3,3-dimethylbutan-2-yl(3-(4-fluorophenyl)-3-hydroxyhex-5-enyl)carba-mate (2.2 g, 6.27 mmol) in dry THF (25 mL) was added NaH (752 mg, 18.80 mmol) at 0° C. under $N_2$, and the mixture was stirred at rt overnight. The reaction was quenched with water, and the mixture was extracted with EtOAc. The combined organic layer was washed with brine, dried over $Na_2SO_4$, filtered and concentrated to afford the crude product, which was purified by chromatography to give two isomers of 6-allyl-3-((2S)-3,3-dimethylbutan-2-yl)-6-(4-fluorophenyl)-1,3-oxazinan-2-one.

Isomer 1: (R)-6-allyl-3-((S)-3,3-dimethylbutan-2-yl)-6-(4-fluorophenyl)-1,3-oxazinan-2-one (450 mg, 20%): NMR ($CDCl_3$): 0.65 (s, 9H), 0.99-1.04 (d, 3H), 1.96-2.05 (m, 1H), 2.21-2.28 (m, 1H), 2.46-2.58 (m, 2H), 2.66-2.75 (m, 1H), 3.08-3.13 (m, 1H), 4.34-4.42 (m, 1H), 4.92-5.04 (m, 2H), 5.61-5.72 (m, 1H), 6.96-7.03 (m, 2H), 7.22-7.28 (m, 2H).

Isomer 2: (S)-6-allyl-3-((S)-3,3-dimethylbutan-2-yl)-6-(4-fluorophenyl)-1,3-oxazinan-2-one (500 mg, 25%): $^1H$ NMR ($CDCl_3$): 0.72-0.93 (m, 12H), 2.11-2.22 (m, 2H), 2.49-2.61 (m, 2H), 2.72-2.82 (m, 1H), 3.08-3.14 (m, 1H), 4.21-4.31 (m, 1H), 4.94-5.04 (m, 2H), 5.61-5.72 (m, 1H), 6.96-7.02 (m, 2H), 7.22-7.25 (m, 2H).

Step 5

A solution of (R)-6-allyl-3-((2S)-3,3-dimethylbutan-2-yl)-6-(4-fluorophenyl)-1,3-oxazinan-2-one [Isomer 1] (450 mg, 1.41 mmol) in dry $CH_2Cl_2$ (10 mL) was treated with $O_3$ at −78° C. till the mixture turned blue. $NaBH_4$ (157 mg, 4.23 mmol) was added, and the mixture was stirred at rt overnight. The solution was concentrated, and the residue was purified by preparative TLC followed by preparative HPLC to give (S)-3-(S)-3,3-dimethylbutan-2-yl)-6-(4-fluorophenyl)-6-(2-hydroxyethyl)-1,3-oxazinan-2-one [Isomer 1] (265 mg, 58%). LC-MS Method 2 $t_R$=3.83, min, m/z=669.03; $^1H$ NMR ($CDCl_3$): 0.71 (s, 9H), 1.06-1.11 (d, 3H), 2.07-2.19 (m, 2H), 2.31-2.28 (m, 1H), 2.67-2.76 (m, 1H), 3.12-3.18 (m, 1H), 3.47-3.58 (m, 1H), 3.69-3.78 (m, 1H), 4.38-4.47 (m, 1H), 7.03-7.09 (m, 2H), 7.26-7.33 (m, 2H).

(S)-6-allyl-3-((2S)-3,3-dimethylbutan-2-yl)-6-(4-fluorophenyl)-1,3-oxazinan-2-one [Isomer 2] (500 mg, 1.57 mmol) was converted to (R)-3-(S)-3,3-dimethylbutan-2-yl)-6-(4-fluorophenyl)-6-(2-hydroxyethyl)-1,3-oxazinan-2-one [Isomer 2] (300 mg, 59%) following a procedure analogous to that described immediately above. LC-MS Method 1 $t_R$=1.112, min, m/z=324.2; $^1H$ NMR ($CDCl_3$): 0.85-0.99 (m, 12H), 2.09-2.18 (m, 1H), 2.19-2.34 (m, 3H), 2.73-2.84 (m, 1H), 3.12-3.28 (m, 1H), 3.48-3.57 (m, 1H), 3.69-3.76 (m, 1H), 4.26-4.35 (m, 1H), 7.02-7.08 (m, 2H), 7.24-7.32 (m, 2H).

EXAMPLE 2

(R)-3-(S)-3,3-dimethylbutan-2-yl)-6-(4-fluorophenyl)-6-(3-hydroxypropyl)-1,3-oxazinan-2-one

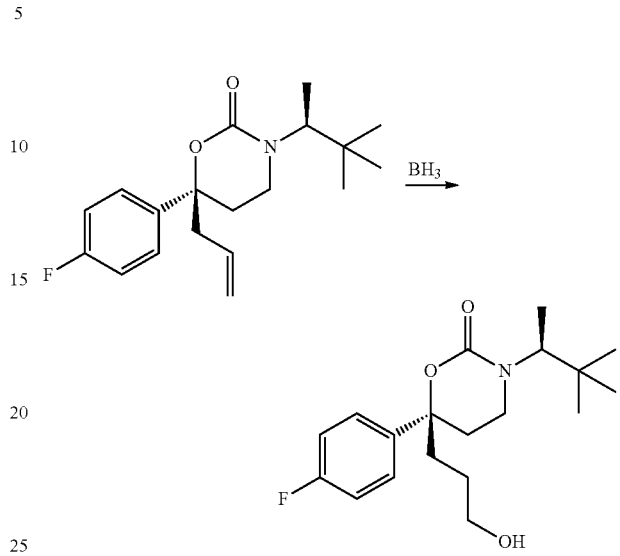

To a solution of (R)-6-allyl-3-((S)-3,3-dimethylbutan-2-yl)-6-(4-fluorophenyl)-1,3-oxazinan-2-one (90 mg, 0.28 mmol) in dry THF (5 mL) was added dropwise 1 M $BH_3$.THF (0.56 mL, 0.564 mmol) at 0° C. After stirring for 2 h at rt, the reaction mixture was cooled to 0° C. and water (1 mL), 3 M aqueous NaOH (0.5 mL) and 30% $H_2O_2$ (0.5 mL) were successively added. The mixture was stirred for 2-3 h at rt and was then diluted with water (6 mL). The pH was adjusted to 6-7 with 0.5 N HCl. The aqueous phase was extracted with EtOAc (3×5 mL). The combined organic layers were washed with saturated aqueous $NaHCO_3$ solution (8 mL) and brine (8 mL), dried over $Na_2SO_4$, and concentrated in vacuo to give the crude product, which was purified by preparative TLC to afford (R)-3-((S)-3,3-dimethylbutan-2-yl)-6-(4-fluorophenyl)-6-(3-hydroxypropyl)-1,3-oxazinan-2-one (2 mg, 2%). LC-MS Method 1 $t_R$=1.179, min, m/z=338.1; $^1H$ NMR ($CDCl_3$) 0.65 (s, 9H), 0.99-1.06 (d, 3H), 1.18 (m, 1H), 1.29 (m, 1H), 1.61-1.71 (m, 1H), 1.83-2.08 (m, 3H), 2.21-2.28 (m, 1H), 2.62-2.73 (m, 1H), 3.06-3.13 (m, 1H), 3.47-3.53 (m, 2H), 4.36-4.43 (m, 1H), 6.98-7.06 (m, 2H), 7.22-7.26 (m, 2H)

EXAMPLE 3

3-((2S)-3,3-dimethylbutan-2-yl)-6-(3-hydroxypropyl)-6-phenyl-1,3-oxazinan-2-one

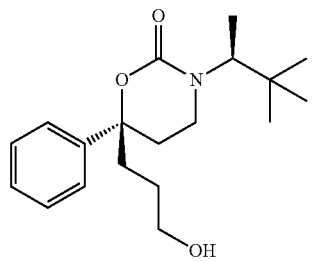 [SMILES: C[C@H](N1CC[C@](CCCO)(c2ccccc2)OC1=O)C(C)(C)C]

The title compound was prepared from 6-allyl-3-((S)-3,3-dimethylbutan-2-yl)-6-phenyl-1,3-oxazinan-2-one following a procedure analogous to that described in EXAMPLE 2 two Isomers were Isolated Isomer 1: (R)-3-(S)-3,3-dimethylbutan-2-yl)-6-(3-hydroxypropyl)-6-phenyl-1,3-oxazinan-2-one. LC-MS Method 1 $t_R$=1.182, min, m/z=320.2; $^1$H NMR (CDCl$_3$) 0.71 (s, 9H), 1.09 (d, 3H), 1.37 (m, 1H), 1.72 (m, 1H), 1.98 (m, 2H), 2.08 (m, 1H), 2.37 (m, 1H), 2.76 (m, 1H), 3.13 (m, 1H), 3.57 (m, 2H), 4.46 (m, 1H), 7.22-7.41 (m, 5H).

Isomer 2: (S)-3-((S)-3,3-dimethylbutan-2-yl)-6-(3-hydroxypropyl)-6-phenyl-1,3-oxazinan-2-one. LC-MS Method 1 $t_R$=1.184, min, m/z=320.2; $^1$H NMR (CDCl$_3$) 0.82 (d, 3H), 0.88 (m, 9H), 1.29 (m, 1H), 1.65 (m, 1H), 1.92-2.03 (m, 2H), 2.17 (m, 2H), 2.74 (m, 1H), 3.08 (m, 1H), 3.51 (m, 2H), 4.28 (m, 1H), 7.23 (m, 3H), 7.31 (m, 2H).

EXAMPLE 4

3-((R)-3-((S)-3,3-dimethylbutan-2-yl)-6-(4-fluorophenyl)-2-oxo-1,3-oxazinan-6-yl)propanamide

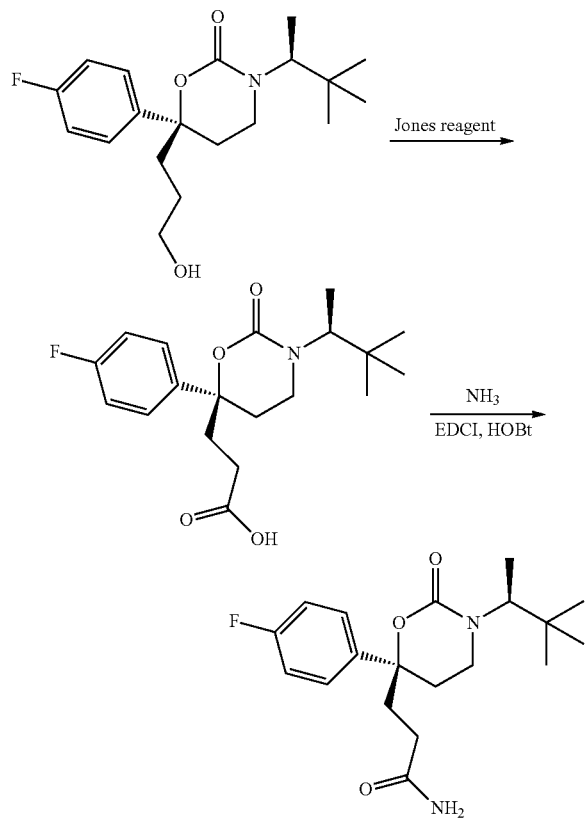

Step 1

To a solution of (R)-3-(S)-3,3-dimethylbutan-2-yl)-6-(4-fluorophenyl)-6-(3-hydroxypropyl)-1,3-oxazinan-2-one (150 mg, 0.45 mmol) in acetone (10 mL) was added Jones reagent (2.5 mol/L, 0.5 mL) at 0° C., and the mixture was stirred at rt for 1 h. The reaction mixture was concentrated, and the mixture was extracted with EtOAc. The combined organic phase was concentrated to give the crude product, which was purified by preparative TLC to give 3-((R)-3-((S)-3,3-dimethylbutan-2-yl)-6-(4-fluorophenyl)-2-oxo-1,3-oxazinan-6-yl)propanoic acid (50 mg, 32%).

Step 2

3-((R)-3-((S)-3,3-dimethylbutan-2-yl)-6-(4-fluorophenyl)-2-oxo-1,3-oxazinan-6-yl)propanoic acid (50 mg, 0.144 mmol), EDCI (55 mg, 0.28 mmol), HOBt (38 mg, 0.28 mmol), and DIEA (90 mg, 0.07 mmol) were dissolved in CH$_2$Cl$_2$ (10 mL) under ice bath. The mixture was stirred under an NH$_3$ atmosphere overnight. The reaction mixture was concentrated to give the crude product, which was purified by preparative TLC to give 3-((R)-3-((S)-3,3-dimethylbutan-2-yl)-6-(4-fluorophenyl)-2-oxo-1,3-oxazinan-6-yl)propanamide (15 mg, 30%). LC-MS Method 1 $t_R$=2.027, min, m/z=351.1; $^1$H NMR (CDCl$_3$) 0.73 (s, 9H), 1.12 (d, 3H), 1.89-1.98 (m, 1H), 2.01-2.12 (m, 1H), 2.22-2.38 (m, 3H), 2.48-2.52 (m, 1H), 2.71 (m, 1H), 3.18 (m, 1H), 4.46 (m, 1H), 5.29 (s, 1H), 5.53 (s, 1H), 7.07 (m, 2H), 7.29 (m, 2H)

EXAMPLE 5

N-(2-((S)-3-((S)-3,3-dimethylbutan-2-yl)-6-(4-fluorophenyl)-2-oxo-1,3-oxazinan-6-yl)ethyl)methanesulfonamide

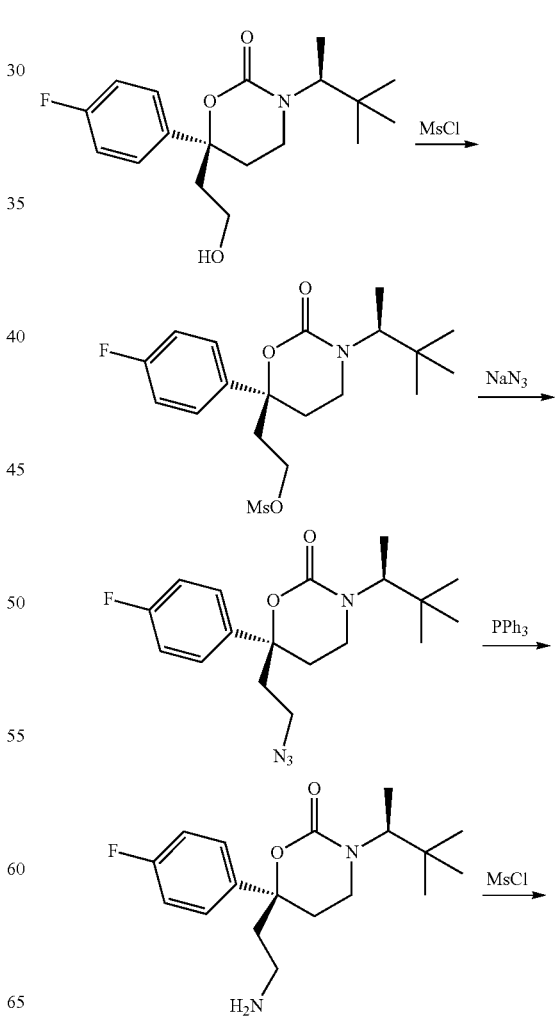

-continued

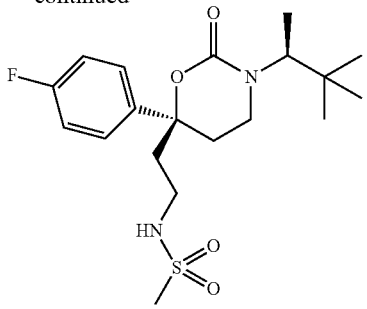

Step 1

To a solution of (S)-3-((S)-3,3-dimethylbutan-2-yl)-6-(4-fluorophenyl)-6-(2-hydroxyethyl)-1,3-oxazinan-2-one (220 mg, 0.68 mmol) and triethylamine (206 mg, 2.04 mmol) in CH$_2$Cl$_2$ (5 mL) was added methanesulfonyl chloride (233 mg, 2.04 mmol) at 0° C., and the reaction mixture was stirred at rt till the reaction was over. The reaction was quenched with H$_2$O. The mixture was extracted with EtOAc, and the organic phase was washed with brine, dried over Na$_2$SO$_4$, filtered and concentrated to give crude 2-((S)-3-((S)-3,3-dimethylbutan-2-yl)-6-(4-fluorophenyl)-2-oxo-1,3-oxazinan-6-yl)ethyl methanesulfonate (280 mg, crude), which was used for the next step without further purification.

Step 2

To a solution of 2-((S)-3-((S)-3,3-dimethylbutan-2-yl)-6-(4-fluorophenyl)-2-oxo-1,3-oxazinan-6-yl)ethyl methanesulfonate (273 mg, 0.68 mmol) in DMF (5 mL) was added NaN$_3$ (133 mg, 2.04 mmol), and the mixture was refluxed overnight. The reaction was quenched with H$_2$O, and the pH of the mixture was adjusted to >9 with 1N aq NaOH. The mixture was extracted with EtOAc (3×). The combined organic layers were washed with water and brine, dried over Na$_2$SO$_4$, filtered and concentrated to give (S)-6-(2-azidoethyl)-3-((S)-3,3-dimethylbutan-2-yl)-6-(4-fluorophenyl)-1,3-oxazinan-2-one (219 mg, 93%). $^1$H NMR (CDCl$_3$): 0.61-0.69 (s, 9H), 1.02-1.08 (d, 3H), 1.98-2.14 (m, 3H), 2.23-2.32 (m, 1H), 2.51-2.61 (m, 1H), 2.91-3.02 (m, 1H), 3.06-3.13 (m, 1H), 3.41-3.52 (m, 1H), 4.33-4.42 (m, 1H), 6.98-7.03 (m, 2H), 7.21-7.24 (m, 2H).

Step 3

To a solution of (S)-6-(2-azidoethyl)-3-((S)-3,3-dimethylbutan-2-yl)-6-(4-fluorophenyl)-1,3-oxazinan-2-one (219 mg, 0.63 mmol) in THF (5 mL) and H$_2$O (0.25 mL) was added PPh$_3$ (198 mg, 0.76 mmol), and the mixture was refluxed for 2 h. The solution was concentrated, and the residue was purified by preparative TLC to afford (R)-6-(2-aminoethyl)-3-((S)-3,3-dimethylbutan-2-yl)-6-(4-fluorophenyl)-1,3-oxazinan-2-one (144 mg, 71%). $^1$H NMR (CDCl$_3$): 0.61-0.69 (s, 9H), 1.02-1.08 (d, 3H), 1.98-2.14 (m, 3H), 2.23-2.31 (m, 1H), 2.48-2.56 (m, 1H), 2.58-2.67 (m, 1H), 2.77-2.86 (m, 1H), 3.07-3.12 (m, 1H), 4.33-4.40 (m, 1H), 6.98-7.04 (m, 2H), 7.21-7.24 (m, 2H).

Step 4

To a solution of (R)-6-(2-aminoethyl)-3-((S)-3,3-dimethylbutan-2-yl)-6-(4-fluorophenyl)-1,3-oxazinan-2-one (144 mg, 0.45 mmol) and triethylamine (136 mg, 1.35 mmol) in CH$_2$Cl$_2$ (5 mL) was added methanesulfonyl chloride (153 mg, 1.35 mmol) at 0° C., and the reaction mixture was stirred at rt until the reaction was over. The reaction was quenched with H$_2$O. The mixture was extracted with EtOAc, and the organic phase was washed with brine, dried over Na$_2$SO$_4$, filtered and concentrated to give crude product, which was purified by preparative TLC to afford N-(2-((S)-3-((S)-3,3-dimethylbutan-2-yl)-6-(4-fluorophenyl)-2-oxo-1,3-oxazinan-6-yl)ethyl)methanesulfonamide (121 mg, 67%). LC-MS Method 1 t$_R$=1.192, min, m/z=401.1; $^1$H NMR (CDCl$_3$): 0.65 (s, 9H), 1.01-1.07 (d, 3H), 1.96-2.06 (m, 1H), 2.12-2.18 (m, 2H), 2.21-2.28 (m, 1H), 2.57-2.66 (m, 1H), 2.78 (s, 3H), 2.85-2.97 (m, 1H), 3.01-3.12 (m, 2H), 4.31-4.39 (m, 1H), 4.64-4.72 (m, 1H), 6.98-7.07 (m, 2H), 7.19-7.24 (m, 2H).

EXAMPLE 6

N-(3-((R)-3-((S)-3,3-dimethylbutan-2-yl)-6-(4-fluorophenyl)-2-oxo-1,3-oxazinan-6-yl)propyl)methanesulfonamide

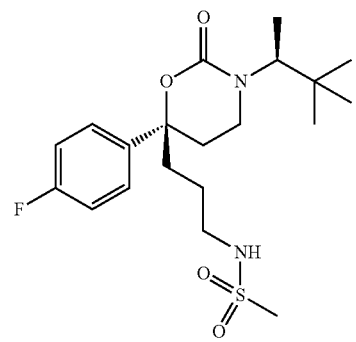 [SMILES: C[C@H](N1CC[C@](CCCNS(C)(=O)=O)(c2ccc(F)cc2)OC1=O)C(C)(C)C]

The title compound was prepared from (R)-3-((S)-3,3-dimethylbutan-2-yl)-6-(4-fluorophenyl)-6-(3-hydroxypropyl)-1,3-oxazinan-2-one following a procedure analogous to that described in Example 6. LC-MS Method 1 t$_R$=1.218, min, m/z=415.2; $^1$H NMR (CDCl$_3$) 0.71 (s, 9H), 1.06-1.11 (d, 3H), 1.29-1.38 (m, 1H), 1.86-2.09 (m, 3H), 2.23-2.31 (m, 1H), 2.63-2.72 (m, 1H), 2.89 (s, 3H), 3.02-3.09 (m, 2H), 3.12-3.17 (m, 1H), 4.39-4.46 (m, 1H), 7.03-7.09 (m, 2H), 7.22-7.27 (m, 2H)

EXAMPLE 7

(S)-1-((S)-3,3-dimethylbutan-2-yl)-4-(4-fluorophenyl)-4-(2-hydroxyethyl)tetrahydropyrimidin-2(1H)-one

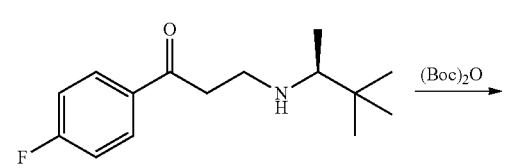

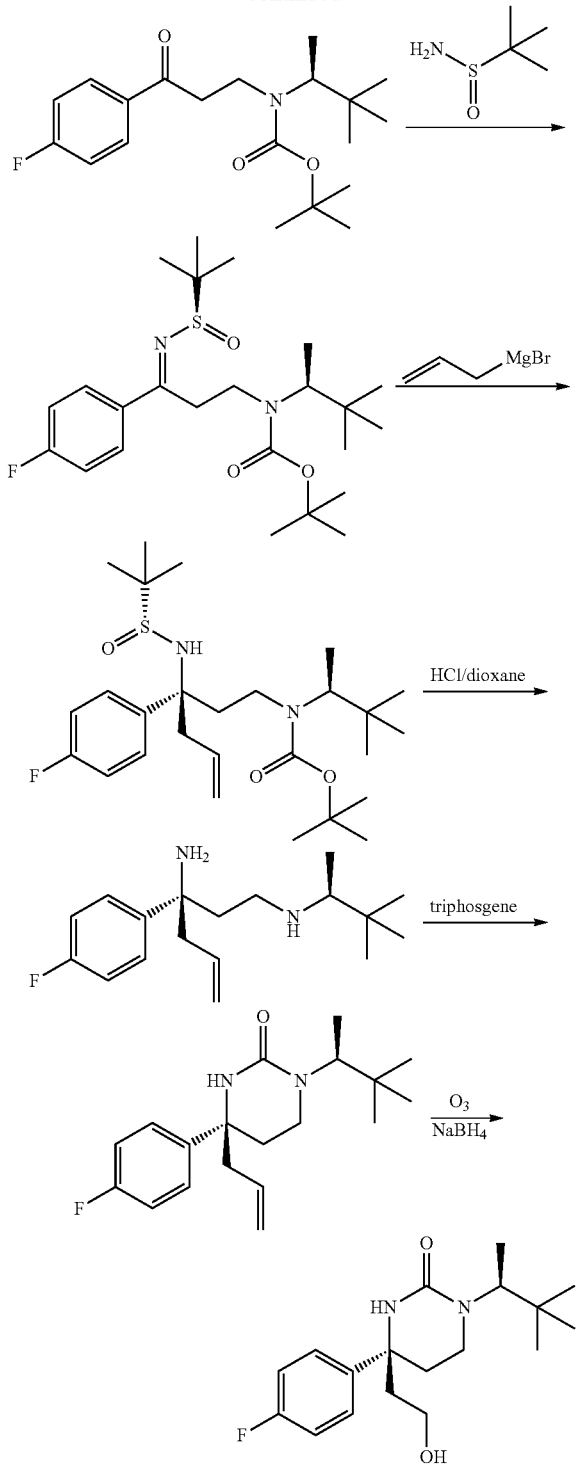

Step 1

To a solution of 3-chloro-1-(4-fluorophenyl)propan-1-one (5.0 g, 0.027 mol) and K$_2$CO$_3$ (7.45 g, 0.054 mol) in acetonitrile (100 mL) was added (S)-3,3-dimethylbutan-2-amine (3.24 g, 0.032 mol), and the reaction mixture was stirred at rt overnight. The solution was filtered, and the filtrate was concentrated to give (S)-3-(3,3-dimethylbutan-2-ylamino)-1-(4-fluorophenyl)propan-1-one (6.40 g, 94%), which was used for the next step without further purification. $^1$H NMR (CDCl$_3$): 0.82 (s, 9H), 0.91-0.96 (d, 3H), 2.14-2.22 (m, 1H), 2.73-2.82 (m, 1H), 3.01-3.11 (m, 3H), 7.01-7.09 (m, 2H), 7.88-7.96 (m, 2H).

Step 2

To a solution of (S)-3-(3,3-dimethylbutan-2-ylamino)-1-(4-fluorophenyl)propan-1-one (2.00 g, 7.97 mmol) and triethylamine (2.41 g, 23.9 mmol) in CH$_2$Cl$_2$ (20 mL) was added di-tert-butyl dicarbonate (4.25 g, 19.5 mmol) dropwise at 0° C., and the reaction mixture was stirred at rt overnight. The solution was washed with 10% citric acid, water and brine. The organic layer was dried over Na$_2$SO$_4$, filtered and concentrated to give the crude product, which was purified by chromatography to afford (S)-tert-butyl 3,3-dimethylbutan-2-yl(3-(4-fluorophenyl)-3-oxopropyl)carbamate (1.50 g, 54%). $^1$H NMR (CDCl$_3$): 0.84 (s, 9H), 1.08 (d, 3H), 1.41 (m, 9H), 3.02 (m, 1H), 3.34 (m, 1H), 3.58 (m, 1H), 3.91-4.15 (m, 1H), 7.01-7.12 (m, 2H), 7.79-8.03 (m, 2H).

Step 3

To a solution of (S)-tert-butyl 3,3-dimethylbutan-2-yl(3-(4-fluorophenyl)-3-oxopropyl)carbamate (1.50 g, 4.27 mmol) in dry THF (20 mL) was added Ti(Oi-Prl)$_4$ (2.46 g, 8.55 mmol) and (R)-2-methylpropane-2-sulfinamide (1.03 g, 8.55 mmol) under N$_2$, and the mixture was refluxed overnight. After the reaction was over, the solution was poured into 20 mL brine and filtered. The filtrate was extracted with EtOAc. The organic layer was washed with brine, dried over Na$_2$SO$_4$, filtered and concentrated to give the crude product, which was purified by chromatography to afford tert-butyl (E)-3-((R)-tert-butylsulfinylimino)-3-(4-fluorophenyl)propyl((S)-3,3-dimethylbutan-2-yl)carbamate (800 mg, 42%). $^1$H NMR (CDCl$_3$): 0.75 (s, 9H), 1.26 (m, 12H), 1.47 (s, 8H), 3.27 (m, 2H), 3.49 (m, 2H), 3.91 (m, 1H), 7.14 (m, 2H), 7.89 (m, 1H), 8.25 (m, 1H).

Step 4

To a solution of tert-butyl (E)-3-((R)-tert-butylsulfinylimino)-3-(4-fluorophenyl)propyl((S)-3,3-dimethylbutan-2-yl)carbamate (800 mg, 1.76 mmol) in THF (10 mL) was added allymagnesium bromide (1 M, 6 mL, 5.29 mmol) dropwise at −78° C. under N$_2$. After adding completely, the reaction mixture was stirred at rt for 2 h. The reaction was quenched with saturated aqueous NH$_4$Cl solution, and the mixture was extracted with EtOAc. The combined organic layer was washed with brine, dried over Na$_2$SO$_4$, filtered and concentrated to give tert-butyl (S)-3,3-dimethylbutan-2-yl ((R)-3-((R)-1,1-dimethylethylsulfinamido)-3-(4-fluorophenyl)hex-5-enyl)carbamate (870 mg, crude), which was used for the next step without further purification.

Step 5

A solution of tert-butyl (S)-3,3-dimethylbutan-2-yl((R)-3-(R)-1,1-dimethylethylsulfinamido)-3-(4-fluorophenyl)hex-5-enyl)carbamate (870 mg, 1.75 mmol) in HCl/dioxane (4M, 10 mL) was stirred at 0° C. overnight. The solution was concentrated to give (R)—N$^1$—((S)-3,3-dimethylbutan-2-yl)-3-(4-fluorophenyl)hex-5-ene-1,3-diamine (600 mg; crude), which was used for the next step.

Step 6

To a solution of (R)—N$^1$—((S)-3,3-dimethylbutan-2-yl)-3-(4-fluorophenyl)hex-5-ene-1,3-diamine (600 mg, 2.05 mmol) and triethylamine (1.04 g, 10.25 mmol) in CH$_2$Cl$_2$ (10 mL) was added triphosgene (203 mg, 0.68 mmol) at 0° C., and the mixture was stirred for 2 h. The reaction was quenched with water, and the mixture was extracted with CH$_2$Cl$_2$. The organic layer was washed with brine, dried over Na$_2$SO$_4$, filtered and concentrated to give the crude product, which was purified by preparative TLC to afford (R)-4-allyl-1-((S)-3,3-dimethylbutan-2-yl)-4-(4-fluorophenyl)tetrahydropyrimidin-2(1H)-one (285 mg, 44%). $^1$H NMR (CDCl$_3$): 0.72 (s, 9H), 1.01 (d, 3H), 1.79 (m, 1H), 2.06 (m, 1H), 2.34 (m, 1H), 2.56 (m, 1H), 2.73 (m, 1H), 3.03 (m, 1H), 4.49 (m, 1H), 4.92 (s, 1H), 5.04-5.13 (m, 2H), 5.26 (m, 1H), 6.95-6.99 (m, 2H), 7.22-7.25 (m, 2H).

Step 7

A solution of (R)-4-allyl-1-((S)-3,3-dimethylbutan-2-yl)-4-(4-fluorophenyl)tetrahydropyrimidin-2(1H)-one (285 mg, 0.90 mmol) in CH$_2$Cl$_2$ (5 mL) was treated with O$_3$ till the mixture was turned blue. Then NaBH$_4$ was added and the mixture was stirred at rt till the reaction was over. The reaction was quenched with H$_2$O, and the mixture was extracted with EtOAc. The organic phase was washed with brine, dried over Na$_2$SO$_4$, filtered and concentrated to give the crude product, which was purified by preparative TLC to afford (S)-1-((S)-3,3-dimethylbutan-2-yl)-4-(4-fluorophenyl)-4-(2-hydroxyethyl)tetrahydropyrimidin-2(1H)-one (120 mg, 42%). LC-MS Method 1 t$_R$=1.021, min, m/z=323.1; $^1$H NMR (CDCl$_3$): 0.72 (s, 9H), 0.99 (d, 3H), 1.35-1.98 (m, 2H), 2.03-2.14 (m, 3H), 2.51 (m, 1H), 3.04 (m, 1H), 3.31 (m, 1H), 3.64 (m, 1H), 4.47 (m, 1H), 6.66 (s, 1H), 6.96-7.01 (m, 2H), 7.24-7.28 (m, 2H).

EXAMPLE 8

3-tert-butyl-6-(3-hydroxypropyl)-6-phenyl-1,3-oxazinan-2-one

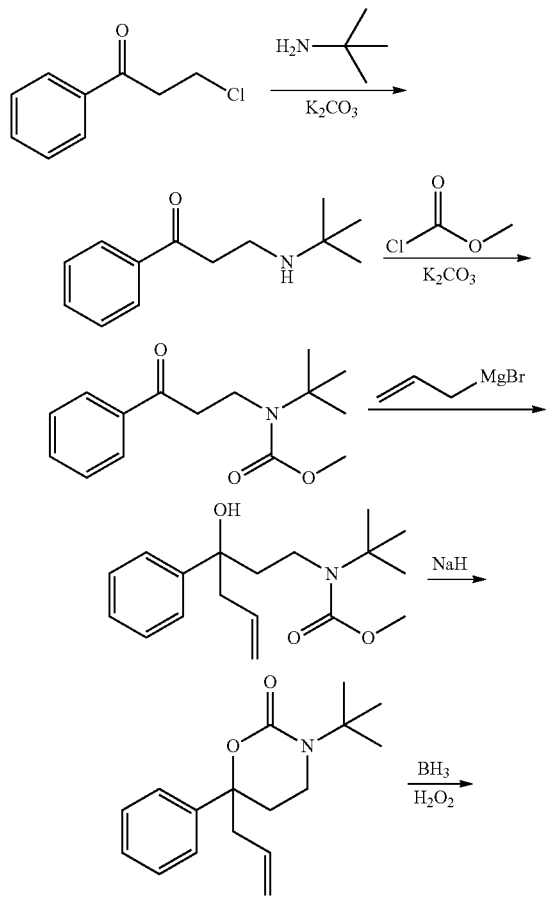

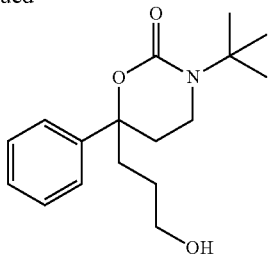

Step 1

To a solution of 3-chloro-1-phenylpropan-1-one (5.0 g, 0.03 mol) and K$_2$CO$_3$ (12.4 g, 0.09 mol) in acetonitrile (100 mL) was added 2-methylpropan-2-amine (4.38 g, 0.06 mol), and the reaction mixture was stirred at rt overnight. The solution was filtered, and the filtrate was concentrated to give 3-(tert-butylamino)-1-phenylpropan-1-one (5.89 g, 96%). $^1$H NMR (CDCl$_3$): 1.01-1.10 (s, 9H), 1.42-1.56 (s, 1H), 2.86-2.92 (m, 2H), 3.09-3.14 (m, 2H), 7.34-7.43 (m, 2H), 7.44-7.51 (m, 1H), 7.85-7.91 (m, 2H).

Step 2

To a solution of 3-(tert-butylamino)-1-phenylpropan-1-one (5.80 g, 0.028 mol) and K$_2$CO$_3$ (7.73 g, 0.056 mol) in CH$_2$Cl$_2$ (100 mL) was added dropwise methyl chloroformate (7.98 g, 0.085 mol) at 0° C., and the reaction mixture was stirred at rt overnight. The solution was filtered. The filtrate was concentrated to give the crude product, which was purified by chromatography to afford methyl tert-butyl(3-oxo-3-phenylpropyl)carbamate (5.09 g, 69%). $^1$H NMR (CDCl$_3$): 1.43 (s, 9H), 3.16-3.21 (m, 2H), 3.62 (s, 3H), 3.60-3.72 (m, 2H), 7.2-7.49 (m, 2H), 7.51-7.59 (m, 1H), 7.93-7.98 (m, 2H).

Step 3

To a solution of methyl tert-butyl(3-oxo-3-phenylpropyl)carbamate (2.0 g, 7.6 mmol) in THF (200 mL) was added allymagnesium bromide (1 M, 23 mL, 23 mmol) dropwise at −78° C. under N$_2$. After adding completely, the reaction mixture was stirred at rt overnight. The reaction was quenched with saturated aqueous NH$_4$Cl solution, and the mixture was extracted with EtOAc. The organic layer was washed with brine, dried over Na$_2$SO$_4$, filtered and concentrated to give the crude product, which was purified by preparative TLC to afford methyl tert-butyl(3-hydroxy-3-phenylhex-5-enyl)carbamate (1.05 g, 46%). $^1$H NMR (CDCl$_3$): 1.12-1.31 (s, 9H), 1.83-1.91 (m, 1H), 2.05-2.11 (m, 1H), 2.38-2.48 (m, 1H), 2.58-2.63 (m, 1H), 2.93-3.01 (m, 1H), 3.21-3.31 (m, 1H), 3.56 (s, 3H), 5.01-5.12 (m, 2H), 5.45-5.56 (m, 1H), 7.15-7.19 (m, 1H), 7.21-7.36 (m, 4H).

Step 4

To a solution of methyl tert-butyl(3-hydroxy-3-phenylhex-5-enyl)carbamate (600 mg, 1.97 mmol) in dry THF (10 mL) was added NaH (236 mg, 5.91 mmol) at 0° C. under N$_2$, and the mixture was stirred at rt overnight. The reaction was quenched with water, and the mixture was extracted with EtOAc. The organic layer was washed with brine, dried over Na$_2$SO$_4$, filtered and concentrated to afford the crude product, which was purified by preparative TLC to give 6-allyl-3-tert-butyl-6-phenyl-1,3-oxazinan-2-one (325 mg, 61%). $^1$H NMR (CDCl$_3$): 1.23 (s, 9H), 2.01-2.21 (m, 1H), 2.28-2.34 (m, 1H), 2.45-2.59 (m, 2H), 2.71-2.81 (m, 1H), 3.13-3.21 (m, 1H), 4.92-5.02 (m, 2H), 5.53-5.63 (m, 1H), 7.21-7.34 (m, 5H).

Step 4

To a solution of 6-allyl-3-tert-butyl-6-phenyl-1,3-oxazinan-2-one (400 mg, 1.46 mmol) in dry THF (10 mL) was added dropwise 1 M of BH$_3$/THF (4.5 mL, 4.40 mmol) at 0°

C. under $N_2$. After stirring at rt for 2 h, the reaction mixture was cooled to 0° C. again, and water (0.1 mL), 3 M of aq NaOH solution (0.1 mL), and 30% $H_2O_2$ (0.3 mL) were added sequentially. After the mixture was stirred at rt for another 2 h, 1 N aq HCl (1.5 mL) was added. The mixture was extracted with EtOAc. The organic layer was washed with brine, dried over $Na_2SO_4$, filtered and concentrated to give the crude product, which was purified by preparative TLC followed by preparative chiral HPLC to afford two isomers of 3-tert-butyl-6-(3-hydroxypropyl)-6-phenyl-1,3-oxazinan-2-one.

Isomer 1 (30 mg, 7%): LC-MS Method 1 $t_R$=1.036, min, m/z=292.1; $^1$H NMR (CDCl$_3$) 1.22-1.48 (m, 10H), 1.59-1.71 (m, 1H), 1.86-1.97 (m, 2H), 2.01-2.15 (m, 1H), 2.22-2.32 (m, 1H), 2.68-2.79 (m, 1H), 3.17-3.25 (m, 1H), 3.47-3.58 (m, 2H), 7.21-7.36 (m, 5H).

Isomer 2 (25 mg, 6%): LC-MS Method 1 $t_R$=1.033, min, m/z=292.1; $^1$H NMR (CDCl$_3$) 1.21-1.38 (m, 10H), 1.61-1.74 (m, 1H), 1.88-2.01 (m, 2H), 2.05-2.16 (m, 1H), 2.24-2.32 (m, 1H), 2.68-2.82 (m, 1H), 3.14-3.26 (m, 1H), 3.48-3.61 (m, 2H), 7.21-7.36 (m, 5H).

EXAMPLE 9

3-tert-butyl-6-(4-fluorophenyl)-6-(3-hydroxypropyl)-1,3-oxazinan-2-one

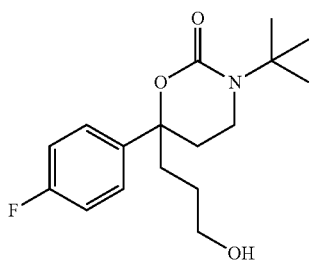 [SMILES: CC(C)(C)N1CCC(CCCO)(c2ccc(F)cc2)OC1=O]

The title compound was prepared from 3-chloro-1-(4-fluorophenyl)propan-1-one following a procedure analogous to that described in Example 8. Two isomers were isolated.

Isomer 1: LC-MS Method 1 $t_R$=2.021, min, m/z=310.2; $^1$H NMR (CDCl$_3$) 1.22-1.39 (m, 10H), 1.56-1.72 (m, 1H), 1.81-1.99 (m, 2H), 2.04-2.13 (m, 1H), 2.19-2.27 (m, 1H), 2.71-2.81 (m, 1H), 3.18-3.24 (m, 1H), 3.46-3.57 (m, 2H), 6.96-7.04 (m, 2H), 7.16-7.26 (m, 2H)

Isomer 2: LC-MS Method 1 $t_R$=2.018, min, m/z=310.2; $^1$H NMR (CDCl$_3$) 1.19-1.34 (m, 10H), 1.52-1.64 (m, 1H), 1.73-1.95 (m, 2H), 2.01-2.12 (m, 1H), 2.13-2.23 (m, 1H), 2.56-2.76 (m, 1H), 3.14-3.23 (m, 1H), 3.41-3.53 (m, 2H), 6.92-7.03 (m, 2H), 7.13-7.22 (m, 2H)

EXAMPLE 10

3-((2S)-3-hydroxy-3-methylbutan-2-yl)-6-(3-hydroxypropyl)-6-phenyl-1,3-oxazinan-2-one

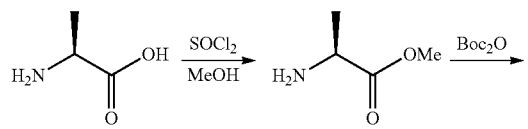

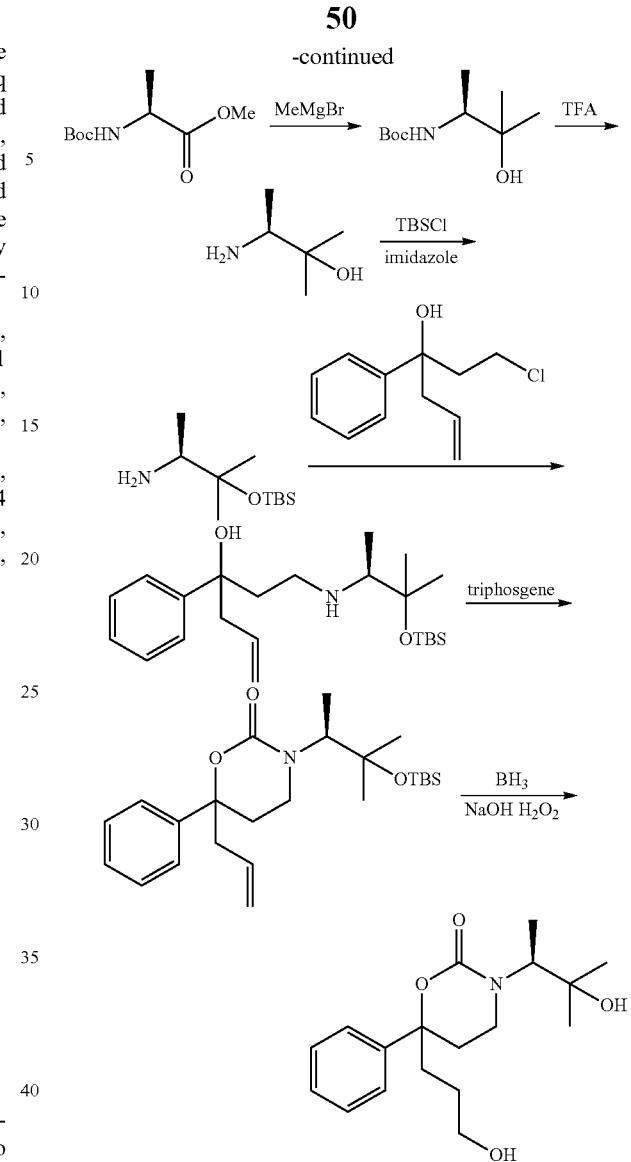

Step 1

To a solution of (S)-2-aminopropanoic acid (30 g, 0.34 mol) in $CH_3OH$ (150 mL) was added $SOCl_2$ (42 mL, 0.58 mol) at 0° C. The formed mixture was stirred overnight. The mixture was concentrated to afford (S)-methyl 2-aminopropanoate (30 g, 86%). $^1$H NMR (CDCl$_3$): 1.27 (d, 3H), 3.52 (q, 1H), 3.68 (s, 3H).

Step 2

To a solution of (S)-methyl 2-aminopropanoate (30 g, 0.29 mol) and $Et_3N$ (88 g, 0.88 mol) in $CH_2Cl_2$ (300 mL) was added (Boc)$_2$O (125 g, 0.58 mol) at 0° C. The formed mixture was stirred overnight. The mixture was filtered and the filtrate was washed with aqueous citric acid. The organic phase was concentrated to give (S)-methyl 2-(tert-butoxycarbonylamino)propanoate (58 g, 100%). $^1$H NMR (CDCl$_3$): 1.27 (d, 3H), 1.39 (s, 9H), 2.83 (q, 1H), 3.71 (s, 3H), 4.28 (brs, 1H), 5.01 (brs, 1H).

Step 3

To a solution of (S)-methyl 2-(tert-butoxycarbonylamino)propanoate (10 g, 0.0493 mol) in THF was added methyl magnesium bromide (100 mL, 3 mol/L) at 0° C. The mixture was stirred for 2 h at rt. The reaction was quenched by addition of a small volume of brine. The mixture was diluted with EtOAc, dried over $Na_2SO_4$, and evaporated to give (S)-tert-butyl 3-hydroxy-3-methylbutan-2-ylcarbamate (10 g, 100%). $^1H$ NMR ($CDCl_3$): 1.08 (d, 3H), 1.11 (s, 3H), 1.18 (s, 3H), 1.39 (s, 9H), 3.52 (brs, 1H), 4.03 (q, 1H), 4.61 (brs, 1H).

Step 4

A mixture of (S)-tert-butyl 3-hydroxy-3-methylbutan-2-ylcarbamate (5 g, 24.6 mmol) in 20% $TFA/CH_2Cl_2$ (30 mL) was stirred for 1 h at 0° C. The mixture was concentrated to afforded (S)-3-amino-2-methylbutan-2-ol (2.5 g, 100%), which was used for the next step without purification. $^1H$ NMR ($CDCl_3$): 1.24 (s, 3H), 1.31 (d, 3H), 1.36 (s, 3H), 3.89 (q, 1H).

Step 5

To a solution of (S)-3-amino-2-methylbutan-2-ol (4 g, 38.8 mmol) and imidazole (5.20 g, 77.7 mmol) in $CH_2Cl_2$ (50 mL) was added TBSCl (8.7 g, 57.7 mmol) at 0° C. The mixture was stirred overnight. The mixture was washed with brine. The organic phase was separated and concentrated to give (S)-3-(tert-butyldimethylsilyloxy)-3-methylbutan-2-amine (8.4 g, 100%), which was used for the next step without purification. $^1H$ NMR ($CDCl_3$): 0.00 (s, 6H), 0.73 (s, 9H), 1.08 (s, 3H), 1.12 (d, 3H), 1.21 (s, 3H), 2.83 (q, 1H), 4.08 (brs, 1H).

Step 6

A mixture of (S)-3-(tert-butyldimethylsilyloxy)-3-methylbutan-2-amine (6 g, 27.6 mmol), 1-chloro-3-phenylhex-5-en-3-ol (4.83 g, 23 mmol) and $K_2CO_3$ (15 g, 100 mmol) in $CH_3CN$ (100 mL) was stirred and heated to reflux overnight. The solid was filtered, and the filtrate was concentrated to give the crude product which was purified by column chromatography to afford 1-((S)-3-(tert-butyldimethylsilyloxy)-3-methylbutan-2-ylamino)-3-phenylhex-5-en-3-ol (300 mg, 3%). $^1H$ NMR ($CDCl_3$): 0.00 (s, 6H), 0.73 (s, 9H), 1.02 (s, 3H), 1.12 (d, 3H), 1.21 (s, 3H), 1.92 (m, 2H), 2.30 (m, 4H), 2.49 (m, 3H), 2.96 (m, 2H), 4.92 (m, 3H), 5.45 (m, 2H), 7.11 (m, 1H), 7.21 (m, 2H), 7.26 (m, 2H).

Step 7

To a solution of 1-((S)-3-(tert-butyldimethylsilyloxy)-3-methylbutan-2-ylamino)-3-phenylhex-5-en-3-ol (550 mg, 1.41 mmol) and $Et_3N$ (1.4 g, 14.1 mmol) in $CH_2Cl_2$ (5 mL) was added triphosgene (138 mg, 0.46 mmol) at 0° C. The formed mixture was heated to reflux overnight. The mixture was washed with water. The organic phase was separated and concentrated to give the crude product which was purified by TLC to afford 6-allyl-3-((2S)-3-(tert-butyldimethylsilyloxy)-3-methylbutan-2-yl)-6-phenyl-1,3-oxazinan-2-one (100 mg, 17%). $^1H$ NMR ($CDCl_3$): 0.00 (s, 6H), 0.73 (s, 9H), 1.08 (s, 3H), 1.12 (d, 3H), 1.21 (s, 3H), 2.83 (q, 1H), 4.08 (brs, 1H).

Step 8

To a solution of 6-allyl-3-((2S)-3-(tert-butyldimethylsilyloxy)-3-methylbutan-2-yl)-6-phenyl-1,3-oxazinan-2-one (300 mg, 0.72 mmol) in THF (5 mL) was added $BH_3$ THF (2.2 mL, 1 mol/L) at 0° C. under nitrogen atmosphere. The formed mixture was stirred for 2 h. The reaction was quenched with water. Then aqueous NaOH solution (1 mol/L, 4.4 mL) and $H_2O_2$ (30%, 2.2 mL) were added to the above mixture. The resulting mixture was stirred for 1.5 h. The mixture was extracted with EtOAc and the combined organic phase was concentrated to give the crude product, which was purified by preparative HPLC to give two isomers of 3-((2S)-3-hydroxy-3-methylbutan-2-yl)-6-(3-hydroxypropyl)-6-phenyl-1,3-oxazinan-2-one.

Isomer 1 (10 mg, 4%): NMR ($CDCl_3$): 1.06 (d, 7H), 1.09 (d, 2H), 1.38 (m, 2H), 1.62 (m, 2H), 1.93 (m, 2H), 2.14 (m, 1H), 2.30 (m, 1H), 2.86 (m, 1H), 3.04-3.20 (m, 2H), 3.50 (t, 2H), 7.23 (m, 3H), 7.34 (m, 2H).

Isomer 2 (12 mg, 5%): $^1H$ NMR ($CDCl_3$): δ=0.99 (s, 3H), 1.03 (m, 1H), 1.14 (s, 3H), 1.20 (d, 3H), 1.28 (m, 1H), 1.63 (m, 1H), 1.92 (m, 2H), 2.19 (m, 1H), 2.29 (m, 1H), 2.86 (m, 1H), 3.24 (m, 1H), 3.50 (t, 2H), 7.23 (m, 3H), 7.33 (m, 2H).

EXAMPLE 11

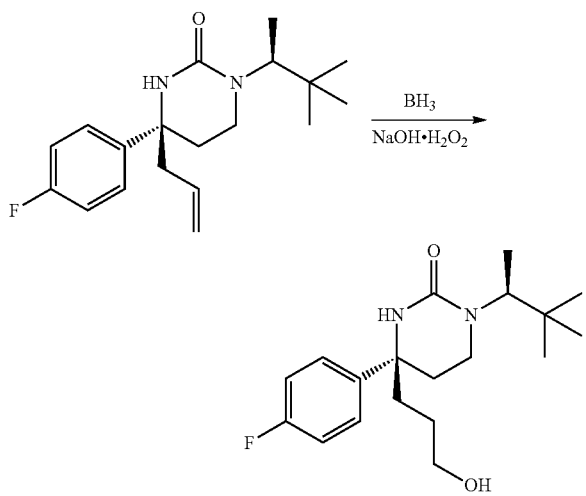

To a solution of (R)-4-allyl-1-((S)-3,3-dimethylbutan-2-yl)-4-(4-fluorophenyl)tetrahydropyrimidin-2(1H)-one (100 mg, 0.31 mmol) in THF (3 mL) was added $BH_3$ THF (1 mL, 1 mol/L) at 0° C. under nitrogen atmosphere. The formed mixture was stirred for 2 h. The reaction was quenched with water. Aqueous NaOH solution (3 mol/L, 0.2 mL) and $H_2O_2$ (30%, 0.2 mL) were added and the resulting mixture was stirred for 1.5 h. The mixture was extracted with ethyl acetate and the combined organic phase was concentrated to give the crude product, which was purified by preparative TLC to give (R)-1-((S)-3,3-dimethylbutan-2-yl)-4-(4-fluorophenyl)-4-(3-hydroxypropyl)tetrahydropyrimidin-2(1H)-one (12 mg, 12%). $^1H$ NMR ($CDCl_3$): 0.73 (s, 3H), 1.04 (d, 3H), 1.29 (m, 1H), 1.48 (m, 1H), 1.81-2.07 (m, 4H), 2.46 (s, 1H), 2.57 (m, 1H), 3.07 (m, 1H), 3.58 (m, 1H), 4.46 (m, 1H), 5.93 (s, 1H), 6.98-7.03 (m, 2H), 7.29 (m, 2H).

EXAMPLE 12

6-allyl-3-((2S)-3-hydroxy-3-methylbutan-2-yl)-6-phenyl-1,3-oxazinan-2-one

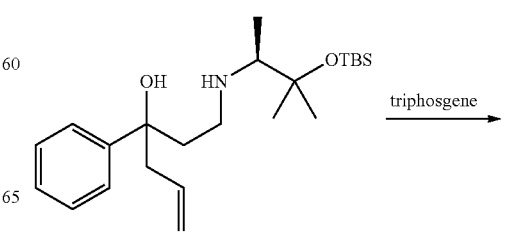

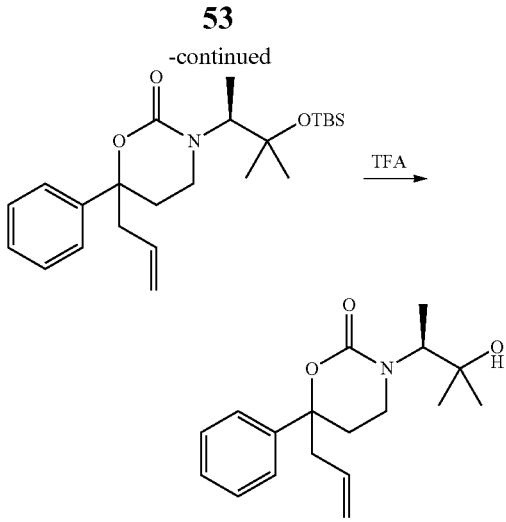

Step 1

To a solution of 1-((S)-3-(tert-butyldimethylsilyloxy)-3-methylbutan-2-ylamino)-3-phenylhex-5-en-3-ol (550 mg, 1.41 mmol) and Et$_3$N (1.4 g, 14.1 mmol) in CH$_2$Cl$_2$ (5 mL) was added triphosgene (138 mg, 0.46 mmol) at 0° C. The formed mixture was heated to reflux overnight. The mixture was washed with water. The organic phase was separated and concentrated to give the crude product, which was purified by TLC to afford two isomers.

6-allyl-3-((S)-3-(tert-butyldimethylsilyloxy)-3-methylbutan-2-yl)-6-phenyl-1,3-oxazinan-2-one isomer 1 (50 mg, 8.6%). $^1$H NMR (CDCl$_3$): 0.00 (s, 6H), 0.73 (s, 9H), 1.08 (s, 3H), 1.12 (d, 3H), 1.21 (s, 3H), 2.83 (q, 1H), 4.08 (br, 1H).

6-allyl-3-((S)-3-(tert-butyldimethylsilyloxy)-3-methylbutan-2-yl)-6-phenyl-1,3-oxazinan-2-one isomer 2 (55 mg, 9%). $^1$H NMR (CDCl$_3$): 0.00 (s, 6H), 0.73 (s, 9H), 0.91 (d, 3H), 1.16 (s, 3H), 1.26 (s, 3H), 2.12 (m, 2H), 2.51-2.71 (m, 4H), 2.99 (m, 6H), 3.59 (m, 1H), 4.19 (m, 1H), 5.00 (m, 3H), 5.66 (m, 1H), 7.23 (m, 3H), 7.31 (m, 2H).

Step 2

A mixture of 6-allyl-3-((S)-3-(tert-butyldimethylsilyloxy)-3-methylbutan-2-yl)-6-phenyl-1,3-oxazinan-2-one isomer 1 (80 mg, 0.19 mmol) in 20% TFA/DCM (2 mL) was stirred for 30 min at 0° C. The mixture was concentrated to give crude 6-allyl-3-((S)-3-hydroxy-3-methylbutan-2-yl)-6-phenyl-1,3-oxazinan-2-one isomer 1 (50 mg, 86%). LC-MS Method 2 t$_R$=1.85 min, m/z=326, 304; $^1$H NMR (CDCl$_3$) 1.07 (m, 6H), 1.18 (s, 3H), 2.15 (m, 1H), 2.25 (m, 1H), 2.58 (m, 2H), 2.90 (m, 1H), 3.08 (m, 1H), 3.20 (m, 1H), 5.02 (m, 2H), 5.68 (m, 1H), 7.22 (3H), 7.31 (2H).

6-allyl-3-((S)-3-hydroxy-3-methylbutan-2-yl)-6-phenyl-1,3-oxazinan-2-one isomer 2 was prepared from 6-allyl-3-((S)-3-(tert-butyldimethylsilyloxy)-3-methylbutan-2-yl)-6-phenyl-1,3-oxazinan-2-one isomer 2 following a procedure analogous to that described above. LC-MS Method 2 t$_R$=1.85 min, m/z=326, 304; $^1$H NMR (CDCl$_3$) 0.96 (s, 3H), 1.07 (s, 3H), 1.13 (m, 3H), 1.50 (1H), 2.10-2.30 (3H), 2.56 (m, 2H), 2.88 (m, 1H), 3.25 (m, 1H), 4.98 (m, 2H), 5.65 (m, 1H), 7.15-7.35 (5H).

BIOLOGICAL TEST EXAMPLE 1

The inhibition of microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxysteroid Dehydrogenase Type 1 in Scintillation Proximity Assay Format. Assay Drug Dev Technol 3 (2005) 377-384). All reactions were carried out at room temperature in 96 well clear flexible PET Microbeta plates (PerkinElmer). The assay begins by dispensing 49 μl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 μL of the test compounds in DMSO previously diluted in half-log increments (8 points) starting at 0.1 mM. After a 10 minute pre-incubation, 50 μL of enzyme solution containing microsomes isolated from CHO cells overexpressing human 11β-HSD1 (10-20 μg/ml of total protein) was added, and the plates were incubated for 90 minutes at room temperature. The reaction was stopped by adding 50 μl of the SPA beads suspension containing 10 μM 18β-glycyrrhetinic acid, 5 mg/ml protein A coated YSi SPA beads (GE Healthcare) and 3.3 μg/ml of anti-cortisol antibody (East Coast Biologics) in Superblock buffer (Bio-Rad). The plates were shaken for 120 minutes at room temperature, and the SPA signal corresponding to [$^3$H]cortisol was measured on a Microbeta plate reader.

BIOLOGICAL TEST EXAMPLE 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% CO$_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% CO$_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 μL. The cells were pre-incubated with serum-free, phenol-red-free medium containing 0.1% (v/v) of DMSO and various concentrations of the test compounds at least 1 h before [$^3$H] cortisone in ethanol (50 Ci/mmol, ARC, Inc.) was added to achieve a final concentration of cortisone of 100 nM. The cells were incubated for 3-4 hrs at 37° C., 5% CO$_2$. Negative controls were incubated without radioactive substrate and received the same amount of [$^3$H] cortisone at the end of the incubation. Formation of [$^3$H] cortisol was monitored by analyzing 25 μL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

TABLE OF BIOLOGICAL ASSAY RESULTS

| Compound | Biological Test Example 1[a] | Average % inhibition at 100 nM |
|---|---|---|
| EXAMPLE 1 Isomer 1 | ++ | 94.4 |
| EXAMPLE 1 Isomer 2 | ++ | 36.5 |
| EXAMPLE 2 | ++ | 98.6 |
| EXAMPLE 3 Isomer 1 | ++ | 94.0 |
| EXAMPLE 3 Isomer 2 | ++ | 58.8 |
| EXAMPLE 4 | ++ | 91.8 |
| EXAMPLE 5 | ++ | 91.0 |
| EXAMPLE 6 | ++ | 95.9 |
| EXAMPLE 7 | ++ | 93.3 |
| EXAMPLE 8 Isomer 1 | ++ | 84.0 |
| EXAMPLE 8 Isomer 2 | # | 22.1 |
| EXAMPLE 9 Isomer 1 | ++ | 74.7 |
| EXAMPLE 9 Isomer 2 | # | 25.45 |
| EXAMPLE 10 Isomer 1 | ++ | 66.8 |
| EXAMPLE 10 Isomer 2 | # | 13.4 |
| EXAMPLE 11 | ++ | 97 |
| EXAMPLE 12 Isomer 1 | # | 47.2 |
| EXAMPLE 12 Isomer 2 | ++ | 53.9 |

[a] ++ means $IC_{50}$ = <100 nM, # means $IC_{50}$ > 100 nM, nt means not tested.

PROPHETIC EXAMPLES

| Prophetic Example No | $R^1$ | $R^{1a}$ | A | E | $R^2$ | $R^3$ | Q |
|---|---|---|---|---|---|---|---|
| 1 | Me | H | —C(Me)$_2$OMe | bond | Ph | HOCH$_2$CH$_2$CH$_2$— | O |
| 2 | Me | H | —C(Me)$_2$OH | bond | Ph | HOCH$_2$CH$_2$CH$_2$— | O |
| 3 | Me | H | —CH$_2$OH | bond | Ph | HOCH$_2$CH$_2$CH$_2$— | O |
| 4 | Me | H | —CH$_2$OMe | bond | Ph | HOCH$_2$CH$_2$CH$_2$— | O |
| 5 | Me | H | —CH$_2$Ot-Bu | bond | Ph | HOCH$_2$CH$_2$CH$_2$— | O |
| 6 | Me | H | —CH$_2$NMe$_2$ | bond | Ph | HOCH$_2$CH$_2$CH$_2$— | O |
| 7 | Me | H | —CH$_2$NHCH$_2$CF$_3$ | bond | Ph | HOCH$_2$CH$_2$CH$_2$— | O |
| 8 | Me | H | —CH$_2$NHAc | bond | Ph | HOCH$_2$CH$_2$CH$_2$— | O |
| 9 | Me | H | —CH$_2$NHC(=O)t-Bu | bond | Ph | HOCH$_2$CH$_2$CH$_2$— | O |
| 10 | Me | H | —CH$_2$NMeSO$_2$i-Pr | bond | Ph | HOCH$_2$CH$_2$CH$_2$— | O |
| 11 | Me | H | —CH$_2$NHC(=O)NMe$_2$ | bond | Ph | HOCH$_2$CH$_2$CH$_2$— | O |
| 12 | Me | H | —CH$_2$NMeCO$_2$Et | bond | Ph | HOCH$_2$CH$_2$CH$_2$— | O |
| 13 | Me | H | —CH$_2$NH(2-pyridyl) | bond | Ph | HOCH$_2$CH$_2$CH$_2$— | O |
| 14 | H | H | —C(Me)$_3$ | bond | 4-F—Ph | H$_2$NC(=O)CH$_2$CH$_2$— | O |
| 15 | H | H | —C(Me)$_2$OMe | bond | 4-F—Ph | H$_2$NC(=O)CH$_2$CH$_2$— | O |
| 16 | H | H | —C(Me)$_2$NHCH$_2$CH$_2$OMe | bond | 4-F—Ph | H$_2$NC(=O)CH$_2$CH$_2$— | O |
| 17 | H | H | —C(Me)$_2$NHC(=O)Et | bond | 4-F—Ph | H$_2$NC(=O)CH$_2$CH$_2$— | O |
| 18 | H | H | —C(Me)$_2$NHSO$_2$Me | bond | 4-F—Ph | H$_2$NC(=O)CH$_2$CH$_2$— | O |
| 19 | H | H | —C(Me)$_2$NHC(=O)NHMe | bond | 4-F—Ph | H$_2$NC(=O)CH$_2$CH$_2$— | O |
| 20 | H | H | —C(Me)$_2$NH(2-pyrimidinyl) | bond | 4-F—Ph | H$_2$NC(=O)CH$_2$CH$_2$— | O |
| 21 | H | H | —CH$_2$SO$_2$i-Pr | bond | 4-F—Ph | H$_2$NC(=O)CH$_2$CH$_2$— | O |
| 22 | Me | H | —CH$_2$C(=O)NEt$_2$ | bond | 2-F—Ph | MeSO$_2$NH(CH$_2$)$_3$— | O |
| 23 | Me | H | —CH$_2$CH$_2$Ot-Bu | bond | 2-F—Ph | MeSO$_2$NH(CH$_2$)$_3$— | O |
| 24 | Me | H | —CH$_2$C(Me$_2$)OH | bond | 2-F—Ph | MeSO$_2$NH(CH$_2$)$_3$— | O |
| 25 | Me | H | —CH$_2$CH$_2$NMeCH$_2$CF$_3$ | bond | 2-F—Ph | MeSO$_2$NH(CH$_2$)$_3$— | O |
| 26 | Me | H | —CH$_2$CH$_2$NHC(=O)i-Pr | bond | 2-F—Ph | MeSO$_2$NH(CH$_2$)$_3$— | O |
| 27 | Me | H | —CH$_2$CH$_2$NHSO$_2$Et | bond | 2-F—Ph | MeSO$_2$NH(CH$_2$)$_3$— | O |
| 28 | Me | H | —CH$_2$CH$_2$NMeC(=O)NMe$_2$ | bond | 2-F—Ph | MeSO$_2$NH(CH$_2$)$_3$— | O |
| 29 | Me | H | —CH$_2$CH$_2$NH(2-pyridyl) | bond | 2-F—Ph | MeSO$_2$NH(CH$_2$)$_3$— | O |
| 30 | Me | H | —CH$_2$CH$_2$SO$_2$Et | bond | 2-F—Ph | MeSO$_2$NH(CH$_2$)$_3$— | O |
| 31 | Me | H | —C(Me)$_2$OMe | bond | Ph | H$_2$NC(=O)CH$_2$CH$_2$— | NH |
| 32 | Me | H | —C(Me)$_2$OH | bond | Ph | H$_2$NC(=O)CH$_2$CH$_2$— | NH |
| 33 | Me | H | —CH$_2$OH | bond | Ph | H$_2$NC(=O)CH$_2$CH$_2$— | NH |
| 34 | Me | H | —CH$_2$OMe | bond | Ph | H$_2$NC(=O)CH$_2$CH$_2$— | NH |
| 35 | Me | H | —CH$_2$Ot-Bu | bond | Ph | H$_2$NC(=O)CH$_2$CH$_2$— | NH |
| 36 | Me | H | —CH$_2$NMe$_2$ | bond | Ph | H$_2$NC(=O)CH$_2$CH$_2$— | NH |
| 37 | Me | H | —CH$_2$NHCH$_2$CF$_3$ | bond | Ph | H$_2$NC(=O)CH$_2$CH$_2$— | NH |
| 38 | Me | H | —CH$_2$NHAc | bond | Ph | H$_2$NC(=O)CH$_2$CH$_2$— | NH |
| 39 | Me | H | —CH$_2$NHC(=O)t-Bu | bond | Ph | H$_2$NC(=O)CH$_2$CH$_2$— | NH |
| 40 | Me | H | —CH$_2$NMeSO$_2$i-Pr | bond | Ph | H$_2$NC(=O)CH$_2$CH$_2$— | NH |
| 41 | Me | H | —CH$_2$NHC(=O)NMe$_2$ | bond | Ph | H$_2$NC(=O)CH$_2$CH$_2$— | NH |
| 42 | Me | H | —CH$_2$NMeCO$_2$Et | bond | Ph | H$_2$NC(=O)CH$_2$CH$_2$— | NH |
| 43 | Me | H | —CH$_2$NH(2-pyridyl) | bond | Ph | H$_2$NC(=O)CH$_2$CH$_2$— | NH |
| 44 | Me | H | —C(Me)$_3$ | bond | 4-F—Ph | MeSO$_2$NH(CH$_2$)$_3$— | NH |
| 45 | Me | H | —C(Me)$_2$OMe | bond | 4-F—Ph | MeSO$_2$NH(CH$_2$)$_3$— | NH |
| 46 | Me | H | —C(Me)$_2$NHCH$_2$CH$_2$OMe | bond | 4-F—Ph | MeSO$_2$NH(CH$_2$)$_3$— | NH |
| 47 | Me | H | —C(Me)$_2$NHC(=O)Et | bond | 4-F—Ph | MeSO$_2$NH(CH$_2$)$_3$— | NH |
| 48 | Me | H | —C(Me)$_2$NHSO$_2$Me | bond | 4-F—Ph | MeSO$_2$NH(CH$_2$)$_3$— | NH |
| 49 | Me | H | —C(Me)$_2$NHC(=O)NHMe | bond | 4-F—Ph | MeSO$_2$NH(CH$_2$)$_3$— | NH |
| 50 | Me | H | —C(Me)$_2$NH(2-pyrimidinyl) | bond | 4-F—Ph | MeSO$_2$NH(CH$_2$)$_3$— | NH |
| 51 | Me | H | —CH$_2$SO$_2$i-Pr | bond | 4-F—Ph | MeSO$_2$NH(CH$_2$)$_3$— | NH |
| 52 | Me | H | —CH$_2$C(=O)NEt$_2$ | bond | 2-F—Ph | HOCH$_2$CH$_2$CH$_2$— | NH |
| 53 | Me | H | —CH$_2$CH$_2$Ot-Bu | bond | 2-F—Ph | HOCH$_2$CH$_2$CH$_2$— | NH |
| 54 | Me | H | —CH$_2$C(Me$_2$)OH | bond | 2-F—Ph | HOCH$_2$CH$_2$CH$_2$— | NH |
| 55 | Me | H | —CH$_2$CH$_2$NMeCH$_2$CF$_3$ | bond | 2-F—Ph | HOCH$_2$CH$_2$CH$_2$— | NH |

-continued

| Prophetic Example No | R¹ | R¹ᵃ | A | E | R² | R³ | Q |
|---|---|---|---|---|---|---|---|
| 56 | Me | H | —CH₂CH₂NHC(=O)i-Pr | bond | 2-F—Ph | HOCH₂CH₂CH₂— | NH |
| 57 | Me | H | —CH₂CH₂NHSO₂Et | bond | 2-F—Ph | HOCH₂CH₂CH₂— | NH |
| 58 | Me | H | —CH₂CH₂NMeC(=O)NMe₂ | bond | 2-F—Ph | HOCH₂CH₂CH₂— | NH |
| 59 | Me | H | —CH₂CH₂NH(2-pyridyl) | bond | 2-F—Ph | HOCH₂CH₂CH₂— | NH |
| 60 | Me | H | —CH₂CH₂SO₂Et | bond | 2-F—Ph | HOCH₂CH₂CH₂— | NH |
| 61 | Me | H | —CF₃ | bond | 2-F—Ph | HOCH₂CH₂CH₂— | O |
| 62 | Me | H | t-Bu | bond | Ph | (R)—MeCH(OH)CH₂— | O |
| 63 | Me | H | t-Bu | bond | Ph | (S)—MeCH(OH)CH₂— | O |
| 64 | Me | H | t-Bu | bond | 4-F—Ph | (R)—MeCH(OH)CH₂— | O |
| 65 | Me | H | t-Bu | bond | 4-F—Ph | (S)—MeCH(OH)CH₂— | O |
| 66 | Me | H | t-Bu | bond | Ph | HOC(Me)₂CH₂— | O |
| 67 | Me | H | t-Bu | bond | 4-F—Ph | HOC(Me)₂CH₂CH₂— | NH |
| 68 | Me | H | t-Bu | bond | Ph | HOCH₂CH(OH)CH₂— | O |
| 69 | Me | H | t-Bu | bond | 4-F—Ph | HOCH₂CH(OH)CH₂— | NH |
| 70 | Me | H | —CH(Et)₂ | bond | 4-F—Ph | HOC(Me)₂CH₂— | O |

The compounds of the invention are useful for ameliorating or treating disorders or diseases in which decreasing the level of cortisol is effective in treating a disease state. Thus, the compounds of the invention can be used in the treatment or prevention of diabetes mellitus, obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. The compounds of the invention can be used as therapeutic agents for pseudo Cushing's Syndrome associated with alcoholic liver disease. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypretriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X. A further disease related to 11β-HSD1 activity is pseudo Cushing's Syndrome associated with alcoholic liver disease.

The disclosed compounds can be used alone (i.e. as a monotherapy) or in combination with another therapeutic agent effective for treating any of the above indications.

A pharmaceutical composition of the invention may, alternatively or in addition to a compound of Formula I, Ia or Ib, comprise a pharmaceutically acceptable salt of a compound of Formula I, Ia or Ib or a prodrug or pharmaceutically active metabolite of such a compound or salt and one or more pharmaceutically acceptable carriers therefore. Alternatively, a pharmaceutical composition of the invention may comprise a compound of Formula I, Ia, or Ib or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

The compositions of the invention are 11β-HSD1 inhibitors. Said compositions contain compounds having a mean inhibition constant ($IC_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of a compound of Formula I, Ia or Ib, or an enantiomer, diastereomer, or pharmaceutically acceptable salt thereof of composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of Formula I, Ia or Ib or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precosee/Glucobay®/Prandase®/Glucore (acarbose, Bayer)

and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of Formula I, Ia or Ib or composition thereof in a combination therapy with one or more other 11β-HSD1 inhibitors (whether such inhibitors are also compounds of Formula I, Ia or Ib or are compounds of a different class/genus), or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

What is claimed is:

1. A compound of Formula (I)

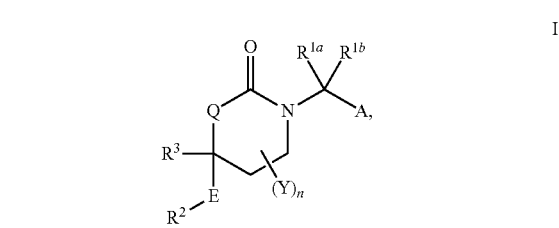

wherein
$R^{1a}$ and $R^{1b}$ are each independently (a) hydrogen or (b) $(C_1-C_6)$alkyl, $(C_2-C_6)$alkenyl, $(C_2-C_6)$alkynyl or $(C_1-C_3)$alkoxy$(C_1-C_3)$alkyl which are optionally substituted with up to three groups independently selected from fluorine, hydroxy, $(C_1-C_3)$alkoxy and $H_2NC(=O)$;

A is straight or branched $(C_1-C_8)$alkyl, $(C_2-C_8)$alkenyl or $(C_2-C_8)$alkynyl, each of which are optionally substituted with up to 4 groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P$ (=O)O, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclylamino (wherein the heterocyclyl portion is optionally substituted by alkyl, haloalkyl or oxo); heteroarylamino (wherein the heteroaryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); arylamino (wherein the aryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and cycloalkylamino (wherein the cycloalkyl portion is optionally substituted by alkyl, haloalkyl or oxo);

Y is $(C_1-C_6)$alkyl or halo$(C_1-C_6)$alkyl;

n is 0;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl, each of which are optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl;

$R^3$ is selected from $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy$(C_1-C_3)$alkoxy, and $(C_1-C_3)$alkoxy$(C_1-C_3)$alkyl, each of which are optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, spirocycloalkyl, heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl; and Q is O;

provided that if (a) Q is O, (b) A is optionally substituted $C_1-C_5$ alkyl; (c) $R^3$ is an optionally substituted $C_1-C_6$ alkyl; (d) then E-$R^2$ is not phenyl substituted with two groups; the two groups being at the meta and para position of the phenyl relative to the point of attachment to the oxazinone ring, wherein the two groups are independently selected from $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy,$(C_1-C_6)$alkoxycarbonyl $(C_1-C_6)$alkoxy, hydroxy$(C_1-C_6)$alkoxy, amino$(C_2-C_6)$alkoxy, $(C_1-C_6)$alkylamino$(C_2-C_6)$alkoxy, and di$(C_1-C_6)$alkylamino$(C_2-C_6)$alkoxy;

or a pharmaceutically acceptable salt, enantiomer or diastereomer thereof.

2. The compound of claim 1 wherein, $R^{1a}$ and $R^{1b}$ are each independently selected from (a) hydrogen or (b) $(C_1-C_6)$alkyl, $(C_2-C_6)$alkenyl, $(C_2-C_6)$alkynyl or $(C_1-C_3)$alkoxy$(C_1-C_3)$alkyl which are optionally substituted with up to three groups independently selected from fluorine, hydroxy, $(C_1-C_3)$alkoxy and $H_2NC(\!=\!O)$;

A is straight or branched $(C_1-C_8)$alkyl, $(C_2-C_8)$alkenyl or $(C_2-C_8)$alkynyl, each of which are optionally substituted with up to 4 groups independently selected from fluorine, cyano, oxo, $R^4$, $R^4O\!-\!$, $(R^4)_2N\!-\!$, $R^4O_2C\!-\!$, $R^4S$, $R^4S(\!=\!O)\!-\!$, $R^4S(\!=\!O)_2\!-\!$, $R^4C(\!=\!O)NR^4\!-\!$, $(R^4)_2NC(\!=\!O)\!-\!$, $(R^4)_2NC(\!=\!O)O\!-\!$, $(R^4)_2NC(\!=\!O)NR^4\!-\!$, $R^4OC(\!=\!O)NR^4\!-\!$, $(R^4)_2NC(\!=\!NCN)NR^4\!-\!$, $(R^4O)_2P(\!=\!O)O$, $(R^4O)_2P(\!=\!O)NR^4\!-\!$, $R^4OS(\!=\!O)_2NR^4\!-\!$, $(R^4)_2NS(\!=\!O)_2O\!-\!$, $(R^4)_2NS(\!=\!O)_2NR^4\!-\!$, $R^4S(\!=\!O)_2NR^4\!-\!$, $R^4S(\!=\!O)_2NHC(\!=\!O)\!-\!$, $R^4S(\!=\!O)_2NHC(\!=\!O)O\!-\!$, $R^4S(\!=\!O)_2NHC(\!=\!O)NR^4\!-\!$, $R^4OS(\!=\!O)_2NHC(\!=\!O)\!-\!$, $R^4OS(\!=\!O)_2NHC(\!=\!O)O\!-\!$, $R^4OS(\!=\!O)_2NHC(\!=\!O)NR^4\!-\!$, $(R^4)_2NS(\!=\!O)_2NHC(\!=\!O)\!-\!$, $(R^4)_2NS(\!=\!O)_2NHC(\!=\!O)O\!-\!$, $(R^4)_2NS(\!=\!O)_2NHC(\!=\!O)NR^4\!-\!$, $R^4C(\!=\!O)NHS(\!=\!O)_2\!-\!$, $R^4C(\!=\!O)NHS(\!=\!O)_2O\!-\!$, $R^4C(\!=\!O)NHS(\!=\!O)_2NR^4\!-\!$, $R^4OC(\!=\!O)NHS(\!=\!O)_2\!-\!$, $R^4OC(\!=\!O)NHS(\!=\!O)_2O\!-\!$, $R^4OC(\!=\!O)NHS(\!=\!O)_2NR^4\!-\!$, $(R^4)_2NC(\!=\!O)NHS(\!=\!O)_2\!-\!$, $(R^4)_2NC(\!=\!O)NHS(\!=\!O)_2O\!-\!$, $(R^4)_2NC(\!=\!O)NHS(\!=\!O)_2NR^4\!-\!$, heterocyclylamino (wherein the heterocyclyl portion is optionally substituted by alkyl, haloalkyl or oxo); heteroarylamino (wherein the heteroaryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); arylamino (wherein the aryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and cycloalkylamino (wherein the cycloalkyl portion is optionally substituted by alkyl, haloalkyl or oxo);

Y is $(C_1-C_6)$alkyl or halo$(C_1-C_6)$alkyl;

n is 0;

E is (a) a bond or (b) $(C_1-C_3)$alkyl or $(C_1-C_2)$alkoxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl each of which are optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

$R^3$ is selected from $(C_1-C_6)$alkyl, $(C_2-C_6)$alkenyl, $(C_2-C_6)$alkynyl and $(C_1-C_3)$alkoxy$(C_1-C_3)$alkyl, each of which are optionally substituted with up to four groups independently selected from fluorine, cyano, oxo, $R^4$, $R^4O\!-\!$, $(R^4)_2N\!-\!$, $R^4O_2C\!-\!$, $R^4S$, $R^4S(\!=\!O)\!-\!$, $R^4S(\!=\!O)_2\!-\!$, $R^4C(\!=\!O)NR^4$, $(R^4)_2NC(\!=\!O)\!-\!$, $(R^4)_2NC(\!=\!O)O\!-\!$, $(R^4)_2NC(\!=\!O)NR^4\!-\!$, $R^4OC(\!=\!O)NR^4\!-\!$, $(R^4)_2NC(\!=\!NCN)NR^4\!-\!$, $(R^4O)_2P(\!=\!O)O\!-\!$, $(R^4O)_2P(\!=\!O)NR^4\!-\!$, $R^4OS(\!=\!O)_2NR^4\!-\!$, $(R^4)_2NS(\!=\!O)_2O\!-\!$, $(R^4)_2NS(\!=\!O)_2NR^4\!-\!$, $R^4S(\!=\!O)_2NR^4\!-\!$, $R^4S(\!=\!O)_2NHC(\!=\!O)\!-\!$, $R^4S(\!=\!O)_2NHC(\!=\!O)O\!-\!$, $R^4S(\!=\!O)_2NHC(\!=\!O)NR^4\!-\!$, $R^4OS(\!=\!O)_2NHC(\!=\!O)\!-\!$, $R^4OS(\!=\!O)_2NHC(\!=\!O)O\!-\!$, $R^4OS(\!=\!O)_2NHC(\!=\!O)NR^4\!-\!$, $(R^4)_2NS(\!=\!O)_2NHC(\!=\!O)\!-\!$, $(R^4)_2NS(\!=\!O)_2NHC(\!=\!O)O\!-\!$, $(R^4)_2NS(\!=\!O)_2NHC(\!=\!O)NR^4\!-\!$, $R^4C(\!=\!O)NHS(\!=\!O)_2\!-\!$, $R^4C(\!=\!O)NHS(\!=\!O)_2O\!-\!$, $R^4C(\!=\!O)NHS(\!=\!O)_2NR^4\!-\!$, $R^4OC(\!=\!O)NHS(\!=\!O)_2\!-\!$, $R^4OC(\!=\!O)NHS(\!=\!O)_2O\!-\!$, $R^4OC(\!=\!O)NHS(\!=\!O)_2NR^4\!-\!$, $(R^4)_2NC(\!=\!O)NHS(\!=\!O)_2\!-\!$, $(R^4)_2NC(\!=\!O)NHS(\!=\!O)_2O\!-\!$, $(R^4)_2NC(\!=\!O)NHS(\!=\!O)_2NR^4\!-\!$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), aryl-amino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl; and Q is O or a pharmaceutically acceptable salt, enantiomer or diastereomer thereof.

3. The compound of claim 2 wherein,

A is straight or branched ($C_1$-$C_8$)alkyl, ($C_2$-$C_8$)alkenyl or ($C_2$-$C_8$)alkynyl, each of which are optionally substituted with up to 4 groups independently selected from fluorine, cyano, $R^4$; $R^4O$—; $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclylamino (wherein the heterocyclyl portion is optionally substituted by alkyl, haloalkyl or oxo); heteroarylamino (wherein the heteroaryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); arylamino (wherein the aryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), and cycloalkylamino (wherein the cycloalkyl portion is optionally substituted by alkyl, haloalkyl or oxo); and $R^3$ is selected from ($C_1$-$C_6$)alkyl, ($C_2$-$C_6$)alkenyl, ($C_2$-$C_6$)alkynyl; ($C_1$-$C_3$)alkoxy($C_2$-$C_3$)alkyl and ($C_2$-$C_3$)alkoxy($C_1$-$C_3$)alkyl wherein each is optionally substituted with up to four groups independently selected from cyano, $R^4$, —OH; $R^4O_2C$—, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

or a pharmaceutucally accptable salt, enantiomer or diastereomer thereof.

4. The compound of claim 2, wherein $R^{1a}$ is methyl or ethyl;

$R^{1b}$ is methyl or hydrogen;

A is methyl, ethyl, isopropyl or t-butyl;

n is 0;

E is a bond or $CH_2$;

$R^2$ is phenyl, thienyl or pyridyl each optionally substituted with halo or methyl; and $R^3$ is methyl, ethyl, n-propyl, n-butyl, i-butyl, i-pentyl, vinyl or allyl each optionally substituted with up to two groups independently selected from HO—, MeO—, $H_2N$—, MeC(=O)NH—, MeS(=O)$_2$NH—, $H_2NC(=O)$, MeNHC(=O)—, $HO_2C$—, $(HO)_2P(=O)O$—, $H_2NS(=O)_2O$—, $H_2NS(=O)_2NH$—, MeNHC(=O)NH—, MeNHC(=O)O— oxo, cyano, $HO_2C$—, $HOCH_2CH_2NH$—, 4-morpholino, $HOCH_2C(=O)NH$—, $H_2NCH_2C(=O)NH$—, EtNHC(=O)NH, MeOC(=O)NH—, MeNHC(=NC≡N)NH—, or oxo.

5. The compound of claim 2, wherein $R^{1a}$ is methyl;

$R^{1b}$ is hydrogen or methyl;

A is methyl or t-butyl;

n is 0;

E is a bond;

$R^2$ is phenyl or 4-fluorophenyl; and $R^3$ is 2-hydroxethyl, 3-hydroxypropyl, 2,3-dihydroxypropyl, $H_2NCOCH_2CH_2$—, $MeSO_2NHCH_2CH_2$—or $MeSO_2NHCH_2CH_2CH_2$—.

6. The compound of claim 1, wherein the compound is represented by Formula Ia:

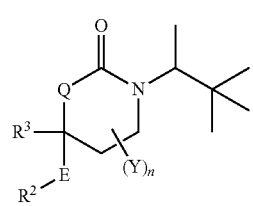

Ia or a pharmaceutically acceptable salt, enantiomer or diastereomer thereof.

7. The compound of claim 2, wherein the compound is represented by Formula Ib:

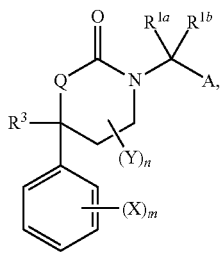

wherein
m is 0, 1, 2, 3 or 4; and
X is independently selected from fluorine, chlorine, bromine, iodine, cyano, nitro, amino, hydroxy, carboxy, $(C_1\text{-}C_6)$alkyl, hydroxy$(C_1\text{-}C_6)$alkyl, $(C_3\text{-}C_6)$cycloalkyl, hydroxy$(C_3\text{-}C_6)$cycloalkyl, $(C_4\text{-}C_7)$cycloalkylalkyl, $(C_2\text{-}C_6)$alkenyl, halo$(C_2\text{-}C_6)$alkenyl, hydroxy$(C_2\text{-}C_6)$alkenyl, $(C_2\text{-}C_6)$alkynyl, $(C_3\text{-}C_6)$cycloalkyl$(C_2\text{-}C_4)$alkynyl, halo$(C_1\text{-}C_6)$alkyl, halo$(C_3\text{-}C_6)$cycloalkyl, halo$(C_4\text{-}C_7)$cycloalkylalkyl, $(C_1\text{-}C_6)$alkoxy, $(C_3\text{-}C_6)$cycloalkoxy, $(C_4\text{-}C_7)$cycloalkylalkoxy, halo$(C_1\text{-}C_6)$alkoxy, halo$(C_3\text{-}C_6)$cycloalkoxy, halo$(C_4\text{-}C_7)$cycloalkylalkoxy, $(C_1\text{-}C_6)$alkylthio, $(C_3\text{-}C_6)$cycloalkylthio, $(C_4\text{-}C_7)$cycloalkylalkylthio, halo$(C_1\text{-}C_6)$alkylthio, halo$(C_3\text{-}C_6)$cycloalkylthio, halo$(C_4\text{-}C_7)$cycloalkylalkylthio, $(C_1\text{-}C_6)$alkanesulfinyl, $(C_3\text{-}C_6)$cycloalkanesulfinyl, $(C_4\text{-}C_7)$cycloalkylalkanesulfinyl, halo$(C_1\text{-}C_6)$alkane-sulfinyl, halo$(C_3\text{-}C_6)$cycloalkanesulfinyl, halo$(C_4\text{-}C_7)$cycloalkylalkanesulfinyl, $(C_1\text{-}C_6)$alkanesulfonyl, $(C_3\text{-}C_6)$cycloalkanesulfonyl, $(C_4\text{-}C_7)$cycloalkylalkanesulfonyl, halo$(C_1\text{-}C_6)$alkanesulfonyl, halo$(C_3\text{-}C_6)$cycloalkanesulfonyl, halo$(C_4\text{-}C_7)$cycloalkylalkanesulfonyl, $(C_1\text{-}C_6)$alkylamino, di$(C_1\text{-}C_6)$alkylamino, $(C_1\text{-}C_6)$alkoxy$(C_1\text{-}C_6)$alkoxy, halo$(C_1\text{-}C_6)$alkoxy$(C_1\text{-}C_6)$alkoxy, $(C_1\text{-}C_6)$alkoxycarbonyl, $H_2NCO$, $H_2NSO_2$, $(C_1\text{-}C_6)$alkylaminocarbonyl, di$(C_1\text{-}C_6)$alkylaminocarbonyl, $(C_1\text{-}C_3)$alkoxy$(C_1\text{-}C_3)$alkylaminocarbonyl, heterocyclylcarbonyl, $(C_1\text{-}C_6)$alkylaminosulfonyl, di$(C_1\text{-}C_6)$alkylaminosulfonyl, heterocyclsulfonyl, $(C_1\text{-}C_6)$alkylcarbonylamino, $(C_1\text{-}C_6)$alkylcarbonylamino$(C_1\text{-}C_6)$alkyl, $(C_1\text{-}C_6)$alkylsulfonylamino, $(C_1\text{-}C_6)$alkylsulfonylamino$(C_1\text{-}C_6)$alkyl, $(C_1\text{-}C_6)$alkoxycarbonyl$(C_1\text{-}C_6)$alkoxy, $(C_1\text{-}C_6)$alkoxy$(C_1\text{-}C_6)$alkyl, halo$(C_1\text{-}C_6)$alkoxy$(C_1\text{-}C_6)$alkyl, hydroxy$(C_1\text{-}C_6)$alkoxy, heteroaryl, oxo, amino$(C_1\text{-}C_6)$alkyl, $(C_1\text{-}C_6)$alkylamino$(C_1\text{-}C_6)$alkyl, di$(C_1\text{-}C_6)$alkylamino$(C_1\text{-}C_6)$alkyl amino$(C_2\text{-}C_6)$alkoxy, $(C_1\text{-}C_6)$alkylamino$(C_2\text{-}C_6)$alkoxy, di$(C_1\text{-}C_6)$alkylamino$(C_2\text{-}C_6)$alkoxy and $(C_1\text{-}C_6)$alkylcarbonyl;
or a pharmaceutically acceptable salt, enantiomer or diastereomer thereof.

8. A pharmaceutical composition comprising: i) the compound of claim 1, or a pharmaceutically acceptable salt, enantiomer or diastereomer thereof and ii) a pharmaceutically acceptable carrier or diluent.

9. The pharmaceutical composition of claim 8, wherein $R^3$ is selected from $(C_1\text{-}C_6)$alkyl, $(C_2\text{-}C_6)$alkenyl, $(C_2\text{-}C_6)$alkynyl; $(C_1\text{-}C_3)$alkoxy$(C_2\text{-}C_3)$alkyl and $(C_2\text{-}C_3)$alkoxy$(C_1\text{-}C_3)$alkyl, wherein each is optionally substituted with up to four groups independently selected from, cyano, $R^4$, —OH, $R^4O_2C$—, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo).

10. A method of treating a subject with a disease associated with the activity or expression of 11β-HSD1, comprising the step of administering to the subject an effective amount of a compound of Formula (I):

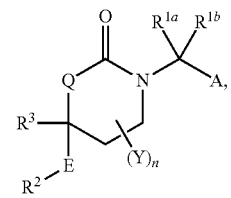

wherein
$R^{1a}$ and $R^{1b}$ are each independently selected from (a) hydrogen or (b) $(C_1\text{-}C_6)$alkyl, $(C_2\text{-}C_6)$alkenyl, $(C_2\text{-}C_6)$alkynyl or $(C_1\text{-}C_3)$alkoxy$(C_1\text{-}C_3)$alkyl which are optionally substituted with up to three groups independently selected from fluorine, hydroxy, $(C_1\text{-}C_3)$alkoxy and $H_2NC(=O)$;
A is straight or branched $(C_1\text{-}C_8)$alkyl, $(C_2\text{-}C_8)$alkenyl or $(C_2\text{-}C_8)$alkynyl, each of which are optionally substituted with up to 4 groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2$ $NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, heterocyclylamino (wherein the heterocyclyl portion is optionally substituted by alkyl, haloalkyl or oxo); heteroarylamino (wherein the heteroaryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (wherein the aryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and cycloalkylamino (wherein the cycloalkyl portion is optionally substituted by alkyl, haloalkyl or oxo);

Y is $(C_1-C_6)$alkyl or halo$(C_1-C_6)$alkyl;

n is 0;

E is (a) a bond or (b) $(C_1-C_3)$alkyl or $(C_1-C_2)$alkoxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl each of wnich are optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

$R^3$ is selected from $(C_1-C_6)$alkyl, $(C_2-C_6)$alkenyl, $(C_2-C_6)$alkynyl and $(C_1-C_3)$alkoxy$(C_1-C_3)$alkyl, each of which are optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl; and Q is O;

or a pharmaceutically acceptable salt, enantiomer or diastereomer thereof, wherein the disease or disorder is selected from diabetes mellitus, obesity, symptoms of metabolic syndrome, glucose intolerance, hyperglycemia, hypertension, hyperlipidemia, insulin resistance, dyslipidemia, atherosclerosis, lipodystrophy, osteoporosis, glaucoma, Cushing's syndrome, Addison's Disease, visreral fat obesity associated with glucocorticoid therapy, depression, anxiety, dementia, cognitive decline, and polycystic ovarian syndrome.

11. A method of treating a subject with a disease or disorder selected from diabetes mellitus, obesity, symptoms of metabolic syndrome, glucose intolerance, hyperglycemia, hypertension, hyperlipidemia, insulin resistance, dyslipidemia, atherosclerosis, lipodystrophy, osteoporosis, glaucoma, Cushing's syndrome, Addison's Disease, visceral fat obesity associated with glucocorticoid therapy, depression, anxiety, dementia, cognitive decline, and polycystic ovarian syndrome, comprising the step of administering to the subject an effective amount of a compound of claim 1.

12. The method of claim 10, wherein $R^{1a}$ is methyl or ethyl;

$R^{1b}$ is methyl or hydrogen;

A is methyl, ethyl, isopropyl or t-butyl;

n is 0;

E is a bond or $CH_2$;

R$^2$ is phenyl, thienyl or pyridyl, each of which are optionally substituted with halo or methyl; and R$^3$ is methyl, ethyl, n-propyl, n-butyl, i-butyl, i-pentyl, vinyl or allyl, each of which are optionally substituted with up to two groups independently selected from HO—, MeO—, H$_2$N—, MeC(=O)NH—, MeS(=O)$_2$NH—, H$_2$NC(=O), MeNHC(=O)—, HO$_2$C—, (HO)$_2$P(=O)O—, H$_2$NS(=O), H$_2$NS(=O)$_2$NH—, MeNHC(=O)NH—, MeNHC(=O)O—oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC=N)NH—, or oxo.

13. The method of claim 10, wherein
R$^{1a}$ is methyl;
R$^{1b}$ is hydrogen or methyl;
A is methyl or t-butyl;
n is 0;
E is a bond;
R$^2$ is phenyl or 4-fluorophenyl; and
R$^3$ is 2-hydroxethyl, 3-hydroxypropyl, 2,3-dihydroxypropyl, H$_2$NCOCH$_2$CH$_2$—, MeSO$_2$NHCH$_2$CH$_2$—or MeSO$_2$NHCH$_2$CH$_2$CH$_2$—.

14. The method of claim 10, wherein the compound is represented by Formula Ia:

Ia or a pharmaceutically acceptable salt, enantiomer or diastereomer thereof.

15. The method of claim 10, wherein the compound is represented Formula Ib:

Ib wherein
m is 0, 1, 2, 3 or 4; and
X is independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkylthio, (C$_4$-C$_7$)cycloalkylalkylthio, halo(C$_1$-C$_6$)alkylthio, halo(C$_3$-C$_6$)cycloalkylthio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkane-sulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cycloalkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxy and (C$_1$-C$_6$)alkylcarbonyl;

or a pharmaceutically acceptable salt, enantiomer or diastereomer thereof.

16. The compound of claim 1, wherein the compound is selected from:
- 3-((2S)-3,3-dimethylbutan-2-yl)-6-(4-fluorophenyl)-6-(2-hydroxyethyl)-1,3-oxazinan-2-one;
- (R)-3-((S)-3,3-dimethylbutan-2-yl)-6-(4-fluorophenyl)-6-(3-hydroxypropyl)-1,3-oxazinan-2-one;
- 3-((2S)-3,3-dimethylbutan-2-yl)-6-(3-hydroxypropyl)-6-phenyl-1,3-oxazinan-2-one;
- 3-((R)-3-((S)-3,3-dimethylbutan-2-yl)-6-(4-fluorophenyl)-2-oxo-1,3-oxazinan-6-yl)propanamide;
- N-(2-((S)-3-((S)-3,3-dimethylbutan-2-yl)-6-(4-fluorophenyl)-2-oxo-1,3-oxazinan-6-yl)ethyl)methanesulfonamide;
- N-(3-((R)-3-((S)-3,3-dimethylbutan-2-yl)-6-(4-fluorophenyl)-2-oxo-1,3-oxazinan-6-yl)propyl)methanesulfonamide;
- 3-tert-butyl-6-(3-hydroxypropyl)-6-phenyl-1,3-oxazinan-2-one;
- 3-tert-butyl-6-(4-fluorophenyl)-6-(3-hydroxypropyl)-1,3-oxazinan-2-one;
- 3-(2S)-3-hydroxy-3-methylbutan-2-yl)-6-(3-hydroxypropyl)-6-phenyl-1,3-oxazinan-2-one; and
- 6-allyl-3-(2S)-3-hydroxy-3-methylbutan-2-yl)-6-phenyl-1,3-oxazinan-2-one;

or a pharmaceutically acceptable salt thereof.

17. A pharmaceutical composition comprising a compound of claim 16, or a pharmaceutically acceptable salt thereof; and a pharmaceutically acceptable carrier or diluent.

18. A method of treating a subject with a disease or disorder selected from diabetes mellitus, obesity, symptoms of metabolic syndrome, glucose intolerance, hyperglycemia, hypertension, hyperlipidemia, insulin resistance, dyslipidemia, atherosclerosis, lipodystrophy, osteoporosis, glaucoma, Cushing's syndrome, Addison's Disease, visceral fat obesity associated with glucocorticoid therapy, depression, anxiety, dementia, cognitive decline, and polycystic ovarian syndrome, comprising the step of administering to the subject an effective amount of a compound of claim 16.

19. The method of claim 18, wherein the disease or disorder is selected from diabetes mellitus, obesity, symptoms of metabolic syndrome, glucose intolerance, hyperglycemia, hypertension, hyperlipidemia, insulin resistance, dyslipidemia, atherosclerosis, lipodystrophy, osteoporosis, glaucoma, Cushing's syndrome, Addison's Disease, visceral fat obesity associated with glucocorticoid therapy, depression, anxiety, dementia, cognitive decline, and polycystic ovarian syndrome.

\* \* \* \* \*

UNITED STATES PATENT AND TRADEMARK OFFICE
CERTIFICATE OF CORRECTION

PATENT NO. : 8,440,658 B2  
APPLICATION NO. : 12/747391  
DATED : May 14, 2013  
INVENTOR(S) : Claremon et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 328 days.

Signed and Sealed this  
Thirtieth Day of December, 2014

Michelle K. Lee  
*Deputy Director of the United States Patent and Trademark Office*